US005856152A

United States Patent [19]
Wilson et al.

[11] Patent Number: 5,856,152
[45] Date of Patent: Jan. 5, 1999

[54] HYBRID ADENOVIRUS-AAV VECTOR AND METHODS OF USE THEREFOR

[75] Inventors: James M. Wilson, Gladwyne, Pa.; William M. Kelley, Ann Arbor, Mich.; Krishna J. Fisher, Philadelphia, Pa.

[73] Assignee: The Trustees of the University of Pennsylvania, Philadelphia, Pa.

[21] Appl. No.: 331,384

[22] Filed: Oct. 28, 1994

[51] Int. Cl.[6] ........................... C12N 15/10; C12N 15/64; C12N 15/86

[52] U.S. Cl. .................. 435/172.3; 435/320.1; 435/369

[58] Field of Search ............................... 435/69.1, 172.3, 435/240.2, 320.1; 424/93.1, 93.2, 93.6

[56] References Cited

U.S. PATENT DOCUMENTS

| | | | |
|---|---|---|---|
| 5,166,320 | 11/1992 | Wu et al. | 530/395 |
| 5,240,846 | 8/1993 | Collins et al. | 435/371 |
| 5,252,479 | 10/1993 | Srivastava | 435/235.1 |
| 5,622,856 | 4/1997 | Natsoulis | 435/325 |

FOREIGN PATENT DOCUMENTS

| | | |
|---|---|---|
| WO91/18088 | 11/1991 | WIPO . |
| WO94/12649 | 6/1994 | WIPO . |
| WO94/13788 | 6/1994 | WIPO . |
| WO94/17832 | 8/1994 | WIPO . |
| WO95/02697 | 1/1995 | WIPO . |
| WO95/13392 | 5/1995 | WIPO . |
| WO95/23867 | 9/1995 | WIPO . |
| WO96/18727 | 6/1996 | WIPO . |

OTHER PUBLICATIONS

Orkin et al. "Report and Recommendations of the Panel to Assess the NIH Investment in Research on Gene Therapy" Dec. 1995.
U. S. Patent Application No. 08/331,381, filed Oct. 28, 1994.
M. Kaplitt et al, "Long–term Gene Expression and Phenotypic Correction Using Adeno–associated Virus Vectors in the Mammalian Brain", *Nat. Genet.*, 8:148–154 (Oct., 1994).
D. Russell et al, "Adeno–associated Virus Vectors Preferentially Transduce Cells in S Phase", *Proc. Natl. Acad. Sci. USA*, 91:8915–8919 (Sep., 1994).
Y. Watanabe, "Serial Inbreeding of Rabbits with Hereditary Hyperlipidemia (WHHL–Rabbit)", *Atherosclerosis*, 36:261–268 (1980).
K. Tanzawa et al, "WHHL–Rabbit: A Low Density Lipoprotein Receptor–Deficient Animal Model for Familial Hypercholesterolemia", *FEBS Letters*, 118(1):81–84 (Aug., 1980).
J. Goldstein et al, "Defective Lipoprotein Receptors and Atherosclerosis—Lessons from an Animal Counterpart of Familial Hypercholesterolemia", *New Engl. J. Med.*, 309(5):288–296 (Aug. 4, 1983).
S. Ishibashi et al, "Hypercholesterolemia in Low Density Lipoprotein Receptor Knockout Mice and its Reversal by Adenovirus–mediated Gene Delivery", *J. Clin. Invest.*, 92:883–893 (Aug., 1993) [Ishibashi I].

S. Ishibashi et al, "Massive Xanthomatosis and Atherosclerosis in Cholesterol–fed Low Density Lipoprotein Receptor–negative Mice", *J. Clin. Invest.*, 93:1885–1893 (May, 1994) [Ishibashi II].
J. Wilson, "Cystic Fibrosis—Vehicles for Gene Therapy", *Nature*, 365:691–692 (Oct. 21, 1993) [Wilson I].
M. Horwitz, "Adenoviridae and Their Replication", 2d edition, ed. B. N. Fields, Raven Press, Ltd., New york, Chapter 60, pp. 1679–1721 (1990).
Y. Yang et al, "Cellular Immunity to Viral Antigens Limits E1–deleted Adenoviruses for Gene Therapy", *Proc. Natl. Acad. Sci. USA*, 91:4407–4411 (May, 1994).
J. Wilson et al, "Correction of the Genetic Defect in Hepatocytes from the Watanabe Heritable Hyperlipidemic Rabbit", *Proc. Natl. Acad. Sci. USA*, 85:4421–4425 (Jun., 1988) [Wilson II].
J. Wilson et al, "Research Article—Transplantation of Allogenic Hepatocytes into LDL Receptor Deficient Rabbits Leads to Transient Improvement in Hypercholesterolemia", *Clin. Bio.*, 3:21–26 (Spring, 1991) [Wilson III].
M. Grossman et al, "Towards Liver–Directed Gene Therapy: Retrovirus–Mediated Gene Transfer into Human Hepatocytes", *Som. Cell. and Mol. Gen.*, 17(6):601–607 (Nov., 1991).
M. Boshart et al, "A Very Strong Enhancer is Located Upstream of an Immediate Early Gene of Human Cytomegalovirus", *Cell*, 41:521–530 (Jun., 1985).
C. Wu et al, "Targeting Genes: Delivery and Persistent Expression of a Foreign Gene Driven by Mammalian Regulatory Elements in vivo", *J. Biol. Chem.*, 264(29):16985–16987 (Oct. 15, 1989).
K. Fisher et al, "Biochemical and Functional Analysis of an Adenovirus–Based Ligand Complex for Gene Transfer", *Biochem. J.*, 299:49–58 (Apr. 1, 1994).
K. Kozarsky et al, "In Vivo Correction of Low–Density Lipoprotein Receptor Deficiency in the Watanabe Heritable Hyperlipidemic Rabbit with Recombinant Adenodviruses", *J. Biol. Chem.*, 269(18):13695–13702 (May 6, 1994).
C. Laughlin et al, "Cloning of Infectious Adeno–associated Virus Genomes in Bacterial Plasmids", *Gene*, 23:65–73 (Jul., 1983).
J. Price et al, "Lineage Analysis in the Vertebrate Nervous System by Retrovirus–mediated Gene Transfer", *Proc. Natl. Acad. Sci. USA*, 84:156–160 (Jan., 1987).

(List continued on next page.)

Primary Examiner—David Guzo
Attorney, Agent, or Firm—Howson and Howson

[57] ABSTRACT

The present invention provides a hybrid vector construct which comprises a portion of an adenovirus, 5' and 3' ITR sequences from an AAV, and a selected transgene. Other hybrid vectors form a polycation conjugate and incorporate an AAV rep gene in a single particle. These hybrid virus vectors are characterized by high titer transgene delivery to a host cell and the ability to stably integrate the transgene into the host cell chromosome. Also disclosed is the use of the hybrid vectors to produce large quantities of recombinant AAV.

8 Claims, 23 Drawing Sheets

OTHER PUBLICATIONS

J. Wilson et al, "A Novel Mechanism for Acheiving Transgene Persistence in vivo after Somatic Gene Transfer into Hepatocytes", *J. Biol. Chem.*, 267(16):11483–11489 (Jun. 5, 1992) [Wilson IV].

T. Kost et al, "The Nucleotide Sequence of the Chick Cytoplasmic beta–actin Gene", *Nucl. Acids Res.*, 11(23):8287–8301 (Dec. 11, 1983).

J. Schreiber et al, "Recombinant Retroviruses Containing Novel Reporter Genes", *BioTechniques*, 14(5):818–823 (May, 1993).

J. Riordan et al, "Identification of the Cystic Fibrosis Gene: Cloning and Characterization of Complementary DNA", *Science*, 245:1066–1073 (Sep. 8, 1989).

M. Brown et al, "A Recceptor–Mediated Pathway for Cholesterol Homeostasis", *Science*, 232:34–46 (Apr. 4, 1986).

T. Yamamoto et al, "The Human LDL Receptor: A Cysteine–Rich Protein with Multiple Alu Sequences in its mRNA", *Cell*, 39:27–38 (Nov., 1984).

R. Samulski et al, "Helper–Free Stocks of Recombinant Adeno–Associated Viruses: Normal Integration does not Require Viral Gene Expression", *J. Virol.*, 63(9):3822–3828 (Sep., 1989).

T. Shenk et al, "Genetic Analysis of Adenoviruses" *Current Topics in Microbiol. and Immunol.*, 111:1–39 (1984).

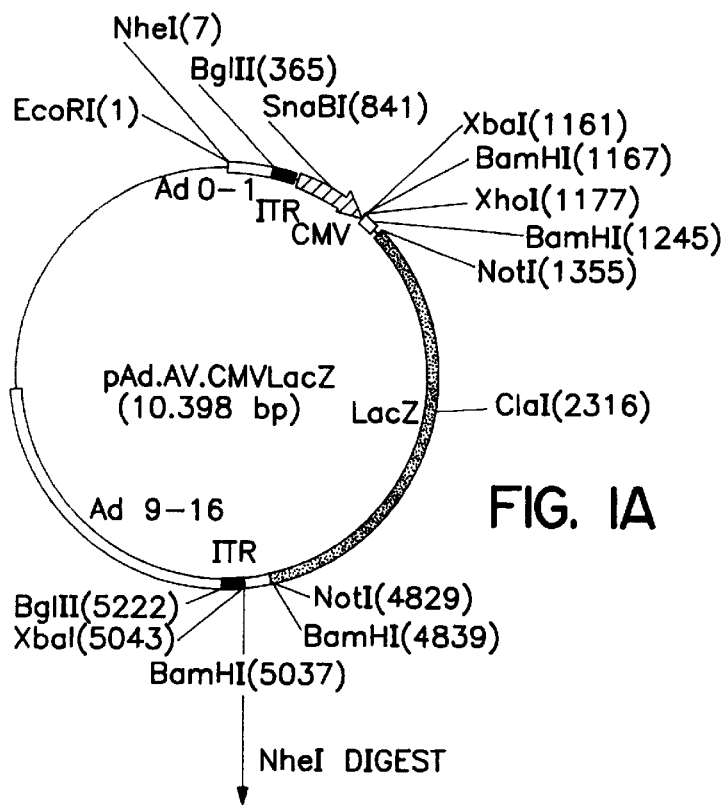
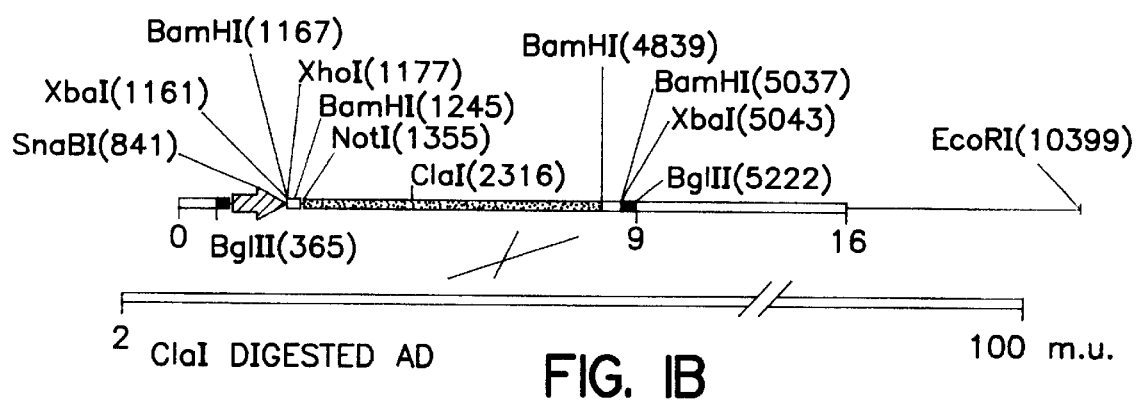
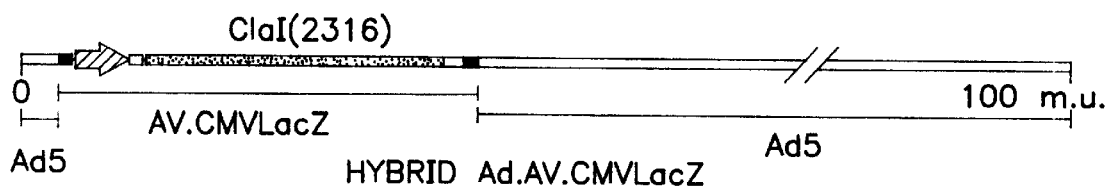
FIG. 1A
FIG. 1B
FIG. 1C

FIGURE 2A

```
GAATTCGCTA GCATCATCAA TAATATACCT TATTTTGGAT TGAAGCCAAT ATGATAATGA
                                                               60

GGGGGTGGAG TTTGTGACGT GGCGCGGGGC GTGGGAACGG GGCGGGTGAC GTAGTAGTGT
                                                              120

GGCGGAAGTG TGATGTTGCA AGTGTGGCGG AACACATGTA AGCGACGGAT GTGGCAAAAG
                                                              180

TGACGTTTTT GGTGTGCGCC GGTGTACACA GGAAGTGACA ATTTTCGCGC GGTTTTAGGC
                                                              240

GGATGTTGTA GTAAATTTGG GCGTAACCGA GTAAGATTTG GCCATTTTCG CGGGAAAACT
                                                              300

GAATAAGAGG AAGTGAAATC TGAATAATTT TGTGTTACTC ATAGCGCGTA ATATTTGTCT
                                                              360

AGGGAGATCT GCTGCGCGCT CGCTCGCTCA CTGAGGCCGC CCGGGCAAAG CCCGGGCGTC
                                                              420

GGGCGACCTT TGGTCGCCCG GCCTCAGTGA GCGAGCGAGC GCGCAGAGAG GGAGTGGCCA
                                                              480

ACTCCATCAC TAGGGGTTCC TTGTAGTTAA TGATTAACCC GCCATGCTAC TTATCTACAA
                                                              540

TTCGAGCTTG CATGCCTGCA GGTCGTTACA TAACTTACGG TAAATGGCCC GCCTGGCTGA
                                                              600

CCGCCCAACG ACCCCGCCC ATTGACGTCA ATAATGACGT ATGTTCCCAT AGTAACGCCA
                                                              660

ATAGGGACTT TCCATTGACG TCAATGGGTG GAGTATTTAC GGTAAACTGC CCACTTGGCA
                                                              720

GTACATCAAG TGTATCATAT GCCAAGTACG CCCCTATTG ACGTCAATGA CGGTAAATGG
                                                              780

CCCGCCTGGC ATTATGCCCA GTACATGACC TTATGGGACT TTCCTACTTG GCAGTACATC
                                                              840

TACGTATTAG TCATCGCTAT TACCATGGTG ATGCGGTTTT GGCAGTACAT CAATGGGCGT
                                                              900

GGATAGCGGT TTGACTCACG GGGATTTCCA AGTCTCCACC CCATTGACGT CAATGGGAGT
                                                              960

TTGTTTTGGC ACCAAAATCA ACGGGACTTT CCAAAATGTC GTAACAACTC CGCCCCATTG
                                                             1020

ACGCAAATGG GCGGTAGGCG TGTACGGTGG GAGGTCTATA TAAGCAGAGC TCGTTTAGTG
                                                             1080
```

FIGURE 2B

```
AACCGTCAGA TCGCCTGGAG ACGCCATCCA CGCTGTTTTG ACCTCCATAG AAGACACCGG
                                                              1140

GACCGATCCA GCCTCCGGAC TCTAGAGGAT CCGGTACTCG AGGAACTGAA AAACCAGAAA
                                                              1200

GTTAACTGGT AAGTTTAGTC TTTTTGTCTT TTATTTCAGG TCCCGGATCC GGTGGTGGTG
                                                              1260

CAAATCAAAG AACTGCTCCT CAGTGGATGT TGCCTTTACT TCTAGGCCTG TACGGAAGTG
                                                              1320

TTACTTCTGC TCTAAAAGCT GCGGAATTGT ACCCGCGGCC GCAATTCCCG GGGATCGAAA
                                                              1380

GAGCCTGCTA AAGCAAAAAA GAAGTCACCA TGTCGTTTAC TTTGACCAAC AAGAACGTGA
                                                              1440

TTTTCGTTGC CGGTCTGGGA GGCATTGGTC TGGACACCAG CAAGGAGCTG CTCAAGCGCG
                                                              1500

ATCCCGTCGT TTTACAACGT CGTGACTGGG AAAACCCTGG CGTTACCCAA CTTAATCGCC
                                                              1560

TTGCAGCACA TCCCCCTTTC GCCAGCTGGC GTAATAGCGA AGAGGCCCGC ACCGATCGCC
                                                              1620

CTTCCCAACA GTTGCGCAGC CTGAATGGCG AATGGCGCTT TGCCTGGTTT CCGGCACCAG
                                                              1680

AAGCGGTGCC GGAAAGCTGG CTGGAGTGCG ATCTTCCTGA GGCCGATACT GTCGTCGTCC
                                                              1740

CCTCAAACTG GCAGATGCAC GGTTACGATG CGCCCATCTA CACCAACGTA ACCTATCCCA
                                                              1800

TTACGGTCAA TCCGCCGTTT GTTCCACGG AGAATCCGAC GGGTTGTTAC TCGCTCACAT
                                                              1860

TTAATGTTGA TGAAAGCTGG CTACAGGAAG GCCAGACGCG AATTATTTTT GATGGCGTTA
                                                              1920

ACTCGGCGTT TCATCTGTGG TGCAACGGGC GCTGGGTCGG TTACGGCCAG GACAGTCGTT
                                                              1980

TGCCGTCTGA ATTTGACCTG AGCGCATTTT TACGCGCCGG AGAAAACCGC CTCGCGGTGA
                                                              2040

TGGTGCTGCG TTGGAGTGAC GGCAGTTATC TGGAAGATCA GGATATGTGG CGGATGAGCG
                                                              2100

GCATTTTCCG TGACGTCTCG TTGCTGCATA AACCGACTAC ACAAATCAGC GATTTCCATG
                                                              2160
```

FIGURE 2C

```
TTGCCACTCG CTTTAATGAT GATTTCAGCC GCGCTGTACT GGAGGCTGAA GTTCAGATGT
                                                                2220

GCGGCGAGTT GCGTGACTAC CTACGGGTAA CAGTTTCTTT ATGGCAGGGT GAAACGCAGG
                                                                2280

TCGCCAGCGG CACCGCGCCT TTCGGCGGTG AAATTATCGA TGAGCGTGGT GGTTATGCCG
                                                                2340

ATCGCGTCAC ACTACGTCTG AACGTCGAAA ACCCGAAACT GTGGAGCGCC GAAATCCCGA
                                                                2400

ATCTCTATCG TGCGGTGGTT GAACTGCACA CCGCCGACGG CACGCTGATT GAAGCAGAAG
                                                                2460

CCTGCGATGT CGGTTTCCGC GAGGTGCGGA TTGAAAATGG TCTGCTGCTG CTAACGGCA
                                                                2520

AGCCGTTGCT GATTCGAGGC GTTAACCGTC ACGAGCATCA TCCTCTGCAT GGTCAGGTCA
                                                                2580

TGGATGAGCA GACGATGGTG CAGGATATCC TGCTGATGAA GCAGAACAAC TTTAACGCCG
                                                                2640

TGCGCTGTTC GCATTATCCG AACCATCCGC TGTGGTACAC GCTGTGCGAC CGCTACGGCC
                                                                2700

TGTATGTGGT GGATGAAGCC AATATTGAAA CCCACGGCAT GGTGCCAATG AATCGTCTGA
                                                                2760

CCGATGATCC GCGCTGGCTA CCGGCGATGA GCGAACGCGT AACGCGAATG GTGCAGCGCG
                                                                2820

ATCGTAATCA CCCGAGTGTG ATCATCTGGT CGCTGGGGAA TGAATCAGGC CACGGCGCTA
                                                                2880

ATCACGACGC GCTGTATCGC TGGATCAAAT CTGTCGATCC TTCCCGCCCG GTGCAGTATG
                                                                2940

AAGGCGGCGG AGCCGACACC ACGGCCACCG ATATTATTTG CCCGATGTAC GCGCGCGTGG
                                                                3000

ATGAAGACCA GCCCTTCCCG GCTGTGCCGA AATGGTCCAT CAAAAAATGG CTTTCGCTAC
                                                                3060

CTGGAGAGAC GCGCCCGCTG ATCCTTTGCG AATACGCCCA CGCGATGGGT AACAGTCTTG
                                                                3120

GCGGTTTCGC TAAATACTGG CAGGCGTTTC GTCAGTATCC CCGTTTACAG GGCGGCTTCG
                                                                3180

TCTGGGACTG GGTGGATCAG TCGCTGATTA AATATGATGA AAACGGCAAC CCGTGGTCGG
                                                                3240
```

FIGURE 2D

```
CTTACGGCGG TGATTTTGGC GATACGCCGA ACGATCGCCA GTTCTGTATG AACGGTCTGG
                                                              3300

TCTTTGCCGA CCGCACGCCG CATCCAGCGC TGACGGAAGC AAAACACCAG CAGCAGTTTT
                                                              3360

TCCAGTTCCG TTTATCCGGG CAAACCATCG AAGTGACCAG CGAATACCTG TTCCGTCATA
                                                              3420

GCGATAACGA GCTCCTGCAC TGGATGGTGG CGCTGGATGG TAAGCCGCTG GCAAGCGGTG
                                                              3480

AAGTGCCTCT GGATGTCGCT CCACAAGGTA AACAGTTGAT TGAACTGCCT GAACTACCGC
                                                              3540

AGCCGGAGAG CGCCGGGCAA CTCTGGCTCA CAGTACGCGT AGTGCAACCG AACGCGACCG
                                                              3600

CATGGTCAGA AGCCGGGCAC ATCAGCGCCT GGCAGCAGTG GCGTCTGGCG GAAAACCTCA
                                                              3660

GTGTGACGCT CCCCGCCGCG TCCCACGCCA TCCCGCATCT GACCACCAGC GAAATGGATT
                                                              3720

TTTGCATCGA GCTGGGTAAT AAGCGTTGGC AATTTAACCG CCAGTCAGGC TTTCTTTCAC
                                                              3780

AGATGTGGAT TGGCGATAAA AAACAACTGC TGACGCCGCT GCGCGATCAG TTCACCCGTG
                                                              3840

CACCGCTGGA TAACGACATT GGCGTAAGTG AAGCGACCCG CATTGACCCT AACGCCTGGG
                                                              3900

TCGAACGCTG GAAGGCGGCG GGCCATTACC AGGCCGAAGC AGCGTTGTTG CAGTGCACGG
                                                              3960

CAGATACACT TGCTGATGCG GTGCTGATTA CGACCGCTCA CGCGTGGCAG CATCAGGGGA
                                                              4020

AAACCTTATT TATCAGCCGG AAAACCTACC GGATTGATGG TAGTGGTCAA ATGGCGATTA
                                                              4080

CCGTTGATGT TGAAGTGGCG AGCGATACAC CGCATCCGGC GCGGATTGGC CTGAACTGCC
                                                              4140

AGCTGGCGCA GGTAGCAGAG CGGGTAAACT GGCTCGGATT AGGGCCGCAA GAAAACTATC
                                                              4200

CCGACCGCCT TACTGCCGCC TGTTTTGACC GCTGGGATCT GCCATTGTCA GACATGTATA
                                                              4260

CCCCGTACGT CTTCCCGAGC GAAAACGGTC TGCGCTGCGG GACGCGCGAA TTGAATTATG
                                                              4320
```

FIGURE 2E

```
GCCCACACCA GTGGCGCGGC GACTTCCAGT TCAACATCAG CCGCTACAGT CAACAGCAAC
                                                                4380

TGATGGAAAC CAGCCATCGC CATCTGCTGC ACGCGGAAGA AGGCACATGG CTGAATATCG
                                                                4440

ACGGTTTCCA TATGGGGATT GGTGGCGACG ACTCCTGGAG CCCGTCAGTA TCGGCGGAAT
                                                                4500

TACAGCTGAG CGCCGGTCGC TACCATTACC AGTTGGTCTG GTGTCAAAAA TAATAATAAC
                                                                4560

CGGGCAGGCC ATGTCTGCCC GTATTTCGCG TAAGGAAATC CATTATGTAC TATTTAAAAA
                                                                4620

ACACAAACTT TTGGATGTTC GGTTTATTCT TTTTCTTTTA CTTTTTTATC ATGGGAGCCT
                                                                4680

ACTTCCCGTT TTTCCCGATT TGGCTACATG ACATCAACCA TATCAGCAAA AGTGATACGG
                                                                4740

GTATTATTTT TGCCGCTATT TCTCTGTTCT CGCTATTATT CCAACCGCTG TTTGGTCTGC
                                                                4800

TTTCTGACAA ACTCGGCCTC GACTCTAGGC GGCCGCGGGG ATCCAGACAT GATAAGATAC
                                                                4860

ATTGATGAGT TTGGACAAAC CACAACTAGA ATGCAGTGAA AAAAATGCTT TATTTGTGAA
                                                                4920

ATTTGTGATG CTATTGCTTT ATTTGTAACC ATTATAAGCT GCAATAAACA AGTTAACAAC
                                                                4980

AACAATTGCA TTCATTTTAT GTTTCAGGTT CAGGGGGAGG TGTGGGAGGT TTTTTCGGAT
                                                                5040

CCTCTAGAGT CGAGTAGATA AGTAGCATGG CGGGTTAATC ATTAACTACA AGGAACCCCT
                                                                5100

AGTGATGGAG TTGGCCACTC CCTCTCTGCG CGCTCGCTCG CTCACTGAGG CCGGGCGACC
                                                                5160

AAAGGTCGCC CGACGCCCGG GCTTTGCCCG GCGGCCTCA GTGAGCGAGC GAGCGCGCAG
                                                                5220

CAGATCTGGA AGGTGCTGAG GTACGATGAG ACCCGCACCA GGTGCAGACC CTGCGAGTGT
                                                                5280

GGCGGTAAAC ATATTAGGAA CCAGCCTGTG ATGCTGGATG TGACCGAGGA GCTGAGGCCC
                                                                5340

GATCACTTGG TGCTGGCCTG CACCCGCGCT GAGTTTGGCT CTAGCGATGA AGATACAGAT
                                                                5400

TGAGGTACTG AAATGTGTGG GCGTGGCTTA AGGGTGGGAA AGAATATATA AGGTGGGGGT
                                                                5460
```

FIGURE 2F

```
CTTATGTAGT TTTGTATCTG TTTTGCAGCA GCCGCCGCCG CCATGAGCAC CAACTCGTTT
                                                                5520
GATGGAAGCA TTGTGAGCTC ATATTTGACA ACGCGCATGC CCCCATGGGC CGGGGTGCGT
                                                                5580
CAGAATGTGA TGGGCTCCAG CATTGATGGT CGCCCCGTCC TGCCCGCAAA CTCTACTACC
                                                                5640
TTGACCTACG AGACCGTGTC TGGAACGCCG TTGGAGACTG CAGCCTCCGC CGCCGCTTCA
                                                                5700
GCCGCTGCAG CCACCGCCCG CGGGATTGTG ACTGACTTTG CTTTCCTGAG CCCGCTTGCA
                                                                5760
AGCAGTGCAG CTTCCCGTTC ATCCGCCCGC GATGACAAGT TGACGGCTCT TTTGGCACAA
                                                                5820
TTGGATTCTT TGACCCGGGA ACTTAATGTC GTTTCTCAGC AGCTGTTGGA TCTGCGCCAG
                                                                5880
CAGGTTTCTG CCCTGAAGGC TTCCTCCCCT CCCAATGCGG TTTAAAACAT AAATAAAAAA
                                                                5940
CCAGACTCTG TTTGGATTTG GATCAAGCAA GTGTCTTGCT GTCTTTATTT AGGGGTTTTG
                                                                6000
CGCGCGCGGT AGGCCCGGGA CCAGCGGTCT CGGTCGTTGA GGGTCCTGTG TATTTTTTCC
                                                                6060
AGGACGTGGT AAAGGTGACT CTGGATGTTC AGATACATGG GCATAAGCCC GTCTCTGGGG
                                                                6120
TGGAGGTAGC ACCACTGCAG AGCTTCATGC TGCGGGGTGG TGTTGTAGAT GATCCAGTCG
                                                                6180
TAGCAGGAGC GCTGGGCGTG GTGCCTAAAA ATGTCTTTCA GTAGCAAGCT GATTGCCAGG
                                                                6240
GGCAGGCCCT TGGTGTAAGT GTTTACAAAG CGGTTAAGCT GGGATGGGTG CATACGTGGG
                                                                6300
GATATGAGAT GCATCTTGGA CTGTATTTTT AGGTTGGCTA TGTTCCCAGC CATATCCCTC
                                                                6360
CGGGGATTCA TGTTGTGCAG AACCACCAGC ACAGTGTATC CGGTGCACTT GGGAAATTTG
                                                                6420
TCATGTAGCT TAGAAGGAAA TGCGTGGAAG AACTTGGAGA CGCCCTTGTG ACCTCCAAGA
                                                                6480
TTTTCCATGC ATTCGTCCAT AATGATGGCA ATGGGCCCAC GGGCGGCGGC CTGGGCGAAG
                                                                6540
```

FIGURE 2G

```
ATATTTCTGG GATCACTAAC GTCATAGTTG TGTTCCAGGA TGAGATCGTC ATAGGCCATT
                                                              6600

TTTACAAAGC GCGGGCGGAG GGTGCCAGAC TGCGGTATAA TGGTTCCATC CGGCCCAGGG
                                                              6660

GCGTAGTTAC CCTCACAGAT TTGCATTTCC CACGCTTTGA GTTCAGATGG GGGGATCATG
                                                              6720

TCTACCTGCG GGGCGATGAA GAAAACGGTT TCCGGGGTAG GGAGATCAG CTGGGAAGAA
                                                              6780

AGCAGGTTCC TGAGCAGCTG CGACTTACCG CAGCCGGTGG GCCCGTAAAT CACACCTATT
                                                              6840

ACCGGGTGCA ACTGGTAGTT AAGAGAGCTG CAGCTGCCGT CATCCCTGAG CAGGGGGGCC
                                                              6900

ACTTCGTTAA GCATGTCCCT GACTCGCATG TTTTCCCTGA CCAAATCCGC CAGAAGGCGC
                                                              6960

TCGCCGCCCA GCGATAGCAG TTCTTGCAAG GAAGCAAAGT TTTTCAACGG TTTGAGACCG
                                                              7020

TCCGCCGTAG GCATGCTTTT GAGCGTTTGA CCAAGCAGTT CCAGGCGGTC CCACAGCTCG
                                                              7080

GTCACCTGCT CTACGGCATC TCGATCCAGC ATATCTCCTC GTTTCGCGGG TTGGGGCGGC
                                                              7140

TTTCGCTGTA CGGCAGTAGT CGGTGCTCGT CCAGACGGGC CAGGGTCATG TCTTTCCACG
                                                              7200

GGCGCAGGGT CCTCGTCAGC GTAGTCTGGG TCACGGTGAA GGGGTGCGCT CCGGGCTGCG
                                                              7260

CGCTGGCCAG GGTGCGCTTG AGGCTGGTCC TGCTGGTGCT GAAGCGCTGC CGGTCTTCGC
                                                              7320

CCTGCGCGTC GGCCAGGTAG CATTTGACCA TGGTGTCATA GTCCAGCCCC TCCGCGGCGT
                                                              7380

GGCCCTTGGC GCGCAGCTTG CCCTTGGAGG AGGCGCCGCA CGAGGGCAG TGCAGACTTT
                                                              7440

TGAGGGCGTA GAGCTTGGGC GCGAGAAATA CCGATTCCGG GGAGTAGGCA TCCGCGCCGC
                                                              7500

AGGCCCCGCA GACGGTCTCG CATTCCACGA GCCAGGTGAG CTCTGGCCGT TCGGGGTCAA
                                                              7560

AAACCAGGTT TCCCCCATGC TTTTTGATGC GTTTCTTACC TCTGGTTTCC ATGAGCCGGT
                                                              7620

GTCCACGCTC GGTGACGAAA AGGCTGTCCG TGTCCCCGTA TACAGACTTG AGAGGCCTGT
                                                              7680
```

FIGURE 2H

```
CCTCGACCGA TGCCCTTGAG AGCCTTCAAC CCAGTCAGCT CCTTCCGGTG GGCGCGGGGC
                                                                 7740
ATGACTATCG TCGCCGCACT TATGACTGTC TTCTTTATCA TGCAACTCGT AGGACAGGTG
                                                                 7800
CCGGCAGCGC TCTGGGTCAT TTTCGGCGAG GACCGCTTTC GCTGGAGCGC GACGATGATC
                                                                 7860
GGCCTGTCGC TTGCGGTATT CGGAATCTTG CACGCCCTCG CTCAAGCCTT CGTCACTGGT
                                                                 7920
CCCGCCACCA AACGTTTCGG CGAGAAGCAG GCCATTATCG CCGGCATGGC GGCCGACGCG
                                                                 7980
CTGGGCTACG TCTTGCTGGC GTTCGCGACG CGAGGCTGGA TGGCCTTCCC CATTATGATT
                                                                 8040
CTTCTCGCTT CCGGCGGCAT CGGGATGCCC GCGTTGCAGG CCATGCTGTC CAGGCAGGTA
                                                                 8100
GATGACGACC ATCAGGGACA GCTTCAAGGA TCGCTCGCGG CTCTTACCAG CCTAACTTCG
                                                                 8160
ATCACTGGAC CGCTGATCGT CACGGCGATT TATGCCGCCT CGGCGAGCAC ATGGAACGGG
                                                                 8220
TTGGCATGGA TTGTAGGCGC CGCCCTATAC CTTGTCTGCC TCCCCGCGTT GCGTCGCGGT
                                                                 8280
GCATGGAGCC GGGCCACCTC GACCTGAATG GAAGCCGGCG GCACCTCGCT AACGGATTCA
                                                                 8340
CCACTCCAAG AATTGGAGCC AATCAATTCT TGCGGAGAAC TGTGAATGCG CAAACCAACC
                                                                 8400
CTTGGCAGAA CATATCCATC GCGTCCGCCA TCTCCAGCAG CCGCACGCGG CGCATCTCGG
                                                                 8460
GCAGCGTTGG GTCCTGGCCA CGGGTGCGCA TGATCGTGCT CCTGTCGTTG AGGACCCGGC
                                                                 8520
TAGGCTGGCG GGGTTGCCTT ACTGGTTAGC AGAATGAATC ACCGATACGC GAGCGAACGT
                                                                 8580
GAAGCGACTG CTGCTGCAAA ACGTCTGCGA CCTGAGCAAC AACATGAATG GTCTTCGGTT
                                                                 8640
TCCGTGTTTC GTAAAGTCTG GAAACGCGGA AGTCAGCGCC CTGCACCATT ATGTTCCGGA
                                                                 8700
TCTGCATCGC AGGATGCTGC TGGCTACCCT GTGGAACACC TACATCTGTA TTAACGAAGC
                                                                 8760
CTTTCTCAAT GCTCACGCTG TAGGTATCTC AGTTCGGTGT AGGTCGTTCG CTCCAAGCTG
                                                                 8820
```

FIGURE 2I

```
GGCTGTGTGC ACGAACCCCC CGTTCAGCCC GACCGCTGCG CCTTATCCGG TAACTATCGT
                                                                8880

CTTGAGTCCA ACCCGGTAAG ACACGACTTA TCGCCACTGG CAGCAGCCAC TGGTAACAGG
                                                                8940

ATTAGCAGAG CGAGGTATGT AGGCGGTGCT ACAGAGTTCT TGAAGTGGTG GCCTAACTAC
                                                                9000

GGCTACACTA GAAGGACAGT ATTTGGTATC TGCGCTCTGC TGAAGCCAGT TACCTTCGGA
                                                                9060

AAAAGAGTTG GTAGCTCTTG ATCCGGCAAA CAAACCACCG CTGGTAGCGG TGGTTTTTTT
                                                                9120

GTTTGCAAGC AGCAGATTAC GCGCAGAAAA AAAGGATCTC AAGAAGATCC TTTGATCTTT
                                                                9180

TCTACGGGGT CTGACGCTCA GTGGAACGAA AACTCACGTT AAGGGATTTT GGTCATGAGA
                                                                9240

TTATCAAAAA GGATCTTCAC CTAGATCCTT TTAAATTAAA AATGAAGTTT TAAATCAATC
                                                                9300

TAAAGTATAT ATGAGTAAAC TTGGTCTGAC AGTTACCAAT GCTTAATCAG TGAGGCACCT
                                                                9360

ATCTCAGCGA TCTGTCTATT TCGTTCATCC ATAGTTGCCT GACTCCCCGT CGTGTAGATA
                                                                9420

ACTACGATAC GGGAGGGCTT ACCATCTGGC CCCAGTGCTG CAATGATACC GCGAGACCCA
                                                                9480

CGCTCACCGG CTCCAGATTT ATCAGCAATA AACCAGCCAG CCGGAAGGGC CGAGCGCAGA
                                                                9540

AGTGGTCCTG CAACTTTATC CGCCTCCATC CAGTCTATTA ATTGTTGCCG GGAAGCTAGA
                                                                9600

GTAAGTAGTT CGCCAGTTAA TAGTTTGCGC AACGTTGTTG CCATTGCTGC AGGCATCGTG
                                                                9660

GTGTCACGCT CGTCGTTTGG TATGGCTTCA TTCAGCTCCG GTTCCCAACG ATCAAGGCGA
                                                                9720

GTTACATGAT CCCCCATGTT GTGCAAAAAA GCGGTTAGCT CCTTCGGTCC TCCGATCGTT
                                                                9780

GTCAGAAGTA AGTTGGCCGC AGTGTTATCA CTCATGGTTA TGGCAGCACT GCATAATTCT
                                                                9840

CTTACTGTCA TGCCATCCGT AAGATGCTTT TCTGTGACTG GTGAGTACTC AACCAAGTCA
                                                                9900
```

FIGURE 2J

TTCTGAGAAT AGTGTATGCG GCGACCGAGT TGCTCTTGCC CGGCGTCAAC ACGGGATAAT
9960

ACCGCGCCAC ATAGCAGAAC TTTAAAAGTG CTCATCATTG GAAAACGTTC TTCGGGGCGA
10020

AAACTCTCAA GGATCTTACC GCTGTTGAGA TCCAGTTCGA TGTAACCCAC TCGTGCACCC
10080

AACTGATCTT CAGCATCTTT TACTTTCACC AGCGTTTCTG GGTGAGCAAA AACAGGAAGG
10140

CAAAATGCCG CAAAAAAGGG AATAAGGGCG ACACGGAAAT GTTGAATACT CATACTCTTC
10200

CTTTTTCAAT ATTATTGAAG CATTTATCAG GGTTATTGTC TCATGAGCGG ATACATATTT
10260

GAATGTATTT AGAAAAATAA ACAAATAGGG GTTCCGCGCA CATTTCCCCG AAAAGTGCCA
10320

CCTGACGTCT AAGAAACCAT TATTATCATG ACATTAACCT ATAAAAATAG GCGTATCACG
10380

AGGCCCTTTC GTCTTCAA
10398

Top　　　　　　　　　Bottom
Gradient Fractions

FIGURE 8A

```
TCGCGCGTTT CGGTGATGAC GGTGAAAACC TCTGACACAT GCAGCTCCCG GAGACGGTCA
                                                                 60
CAGCTTGTCT GTAAGCGGAT GCCGGGAGCA GACAAGCCCG TCAGGGCGCG TCAGCGGGTG
                                                                120
TTGGCGGGTG TCGGGCTGG CTTAACTATG CGGCATCAGA GCAGATTGTA CTGAGAGTGC
                                                                180
ACCATATGCG GTGTGAAATA CCGCACAGAT GCGTAAGGAG AAAATACCGC ATCAGGCGCC
                                                                240
ATTCGCCATT CAGGCTGCGC AACTGTTGGG AAGGGCGATC GGTGCGGGCC TCTTCGCTAT
                                                                300
TACGCCAGCT GGCGAAAGGG GGATGTGCTG CAAGGCGATT AAGTTGGGTA ACGCCAGGGT
                                                                360
TTTCCCAGTC ACGACGTTGT AAAACGACGG CCAGTGCCAA GCTTGCATGC CTGCAGGTCG
                                                                420
ACTCTAGAGG ATCCGAAAAA ACCTCCCACA CCTCCCCCTG AACCTGAAAC ATAAAATGAA
                                                                480
TGCAATTGTT GTTGTTAACT TGTTTATTGC AGCTTATAAT GGTTACAAAT AAAGCAATAG
                                                                540
CATCACAAAT TTCACAAATA AAGCATTTTT TTCACTGCAT TCTAGTTGTG GTTTGTCCAA
                                                                600
ACTCATCAAT GTATCTTATC ATGTCTGGAT CCCCGCGGCC GCCAAATCAT TTATTGTTCA
                                                                660
AAGATGCAGT CATCCAAATC CACATTGACC AGATCGCAGG CAGTGCAAGC GTCTGGCACC
                                                                720
TTTCCCATGA TATGATGAAT GTAGCACAGT TTCTGATACG CCTTTTTGAC GACAGAAACG
                                                                780
GGTTGAGATT CTGACACGGG AAAGCACTCT AAACAGTCTT TCTGTCCGTG AGTGAAGCAG
                                                                840
ATATTTGAAT TCTGATTCAT TCTCTCGCAT TGTCTGCAGG GAAACAGCAT CAGATTCATG
                                                                900
CCCACGTGAC GAGAACATTT GTTTTGGTAC CTGTCTGCGT AGTTGATCGA AGCTTCCGCG
                                                                960
TCTGACGTCG ATGGCTGCGC AACTGACTCG CGCACCCGTT TGGGCTCACT TATATCTGCG
                                                               1020
TCACTGGGGG CGGGTCTTTT CTTGGCTCCA CCCTTTTTGA CGTAGAATTC ATGCTCCACC
                                                               1080
```

FIGURE 8B

```
TCAACCACGT GATCCTTTGC CCACCGGAAA AAGTCTTTGA CTTCCTGCTT GGTGACCTTC
                                                                1140

CCAAAGTCAT GATCCAGACG GCGGGTGAGT TCAAATTTGA ACATCCGGTC TTGCAACGGC
                                                                1200

TGCTGGTGTT CGAAGGTCGT TGAGTTCCCG TCAATCACGG CGCACATGTT GGTGTTGGAG
                                                                1260

GTGACGATCA CGGGAGTCGG GTCTATCTGG GCCGAGGACT TGCATTTCTG GTCCACGCGC
                                                                1320

ACCTTGCTTC CTCCGAGAAT GGCTTTGGCC GACTCCACGA CCTTGGCGGT CATCTTCCCC
                                                                1380

TCCTCCCACC AGATCACCAT CTTGTCGACA CAGTCGTTGA AGGGAAAGTT CTCATTGGTC
                                                                1440

CAGTTTACGC ACCCGTAGAA GGGCACAGTG TGGGCTATGG CCTCCGCGAT GTTGGTCTTC
                                                                1500

CCGGTAGTTG CAGGCCCAAA CAGCCAGATG GTGTTCCTCT TGCCGAACTT TTTCGTGGCC
                                                                1560

CATCCCAGAA AGACGGAAGC CGCATATTGG GGATCGTACC CGTTTAGTTC CAAAATTTTA
                                                                1620

TAAATCCGAT TGCTGGAAAT GTCCTCCACG GGCTGCTGGC CCACCAGGTA GTCGGGGGCG
                                                                1680

GTTTTAGTCA GGCTCATAAT CTTTCCCGCA TTGTCCAAGG CAGCCTTGAT TTGGGACCGC
                                                                1740

GAGTTGGAGG CCGCATTGAA GGAGATGTAT GAGGCCTGGT CCTCCTGGAT CCACTGCTTC
                                                                1800

TCCGAGGTAA TCCCCTTGTC CACGAGCCAC CCGACCAGCT CCATGTACCT GGCTGAAGTT
                                                                1860

TTTGATCTGA TCACCGGCGC ATCAGAATTG GGATTCTGAT TCTCTTTGTT CTGCTCCTGC
                                                                1920

GTCTGCGACA CGTGCGTCAG ATGCTGCGCC ACCAACCGTT TACGCTCCGT GAGATTCAAA
                                                                1980

CAGGCGCTTA AATACTGTTC CATATTAGTC CACGCCCACT GGAGCTCAGG CTGGGTTTTG
                                                                2040

GGGAGCAAGT AATTGGGGAT GTAGCACTCA TCCACCACCT TGTTCCCGCC TCCGGCGCCA
                                                                2100

TTTCTGGTCT TTGTGACCGC GAACCAGTTT GGCAAAGTCG GCTCGATCCC GCGGTAAATT
                                                                2160
```

FIGURE 8C

```
CTCTGAATCA GTTTTTCGCG AATCTGACTC AGGAAACGTC CCAAAACCAT GGATTTCACC
                                                                2220

CCGGTGGTTT CCACGAGCAC GTGCATGTGG AAGTAGCTCT CTCCCTTCTC AAATTGCACA
                                                                2280

AAGAAAAGGG CCTCCGGGGC CTTACTCACA CGGCGCCATT CCGTCAGAAA GTCGCGCTGC
                                                                2340

AGCTTCTCGG CCACGGTCAG GGGTGCCTGC TCAATCAGAT TCAGATCCAT GTCAGAATCT
                                                                2400

GGCGGCAACT CCCATTCCTT CTCGGCCACC CAGTTCACAA AGCTGTCAGA AATGCCGGGC
                                                                2460

AGATGCCCGT CAAGGTCGCT GGGGACCTTA ATCACAATCT CGTAAAACCC CGGCATGGCG
                                                                2520

GCTGCGCGTT CAAACCTCCC GCTTCAAAAT GGAGACCCTG CGTGCTCACT CGGGCTTAAA
                                                                2580

TACCCAGCGT GACCACATGG TGTCGCAAAA TGTCGCAAAA CACTCACGTG ACCTCTAATA
                                                                2640

CAGGACTCTA GAGGATCCCC GGGTACCGAG CTCGAATTCG TAATCATGGT CATAGCTGTT
                                                                2700

TCCTGTGTGA AATTGTTATC CGCTCACAAT TCCACACAAC ATACGAGCCG GAAGCATAAA
                                                                2760

GTGTAAAGCC TGGGGTGCCT AATGAGTGAG CTAACTCACA TTAATTGCGT TGCGCTCACT
                                                                2820

GCCCGCTTTC CAGTCGGGAA ACCTGTCGTG CCAGCTGCAT TAATGAATCG GCCAACGCGC
                                                                2880

GGGGAGAGGC GGTTTGCGTA TTGGGCGCTC TTCCGCTTCC TCGCTCACTG ACTCGCTGCG
                                                                2940

CTCGGTCGTT CGGCTGCGGC GAGCGGTATC AGCTCACTCA AAGGCGGTAA TACGGTTATC
                                                                3000

CACAGAATCA GGGGATAACG CAGGAAAGAA CATGTGAGCA AAAGGCCAGC AAAAGGCCAG
                                                                3060

GAACCGTAAA AAGGCCGCGT TGCTGGCGTT TTTCCATAGG CTCCGCCCCC CTGACGAGCA
                                                                3120

TCACAAAAAT CGACGCTCAA GTCAGAGGTG GCGAAACCCG ACAGGACTAT AAAGATACCA
                                                                3180

GGCGTTTCCC CCTGGAAGCT CCCTCGTGCG CTCTCCTGTT CCGACCCTGC CGCTTACCGG
                                                                3240
```

FIGURE 8D

ATACCTGTCC GCCTTTCTCC CTTCGGGAAG CGTGGCGCTT TCTCATAGCT CACGCTGTAG
3300

GTATCTCAGT TCGGTGTAGG TCGTTCGCTC CAAGCTGGGC TGTGTGCACG AACCCCCCGT
3360

TCAGCCCGAC CGCTGCGCCT TATCCGGTAA CTATCGTCTT GAGTCCAACC CGGTAAGACA
3420

CGACTTATCG CCACTGGCAG CAGCCACTGG TAACAGGATT AGCAGAGCGA GGTATGTAGG
3480

CGGTGCTACA GAGTTCTTGA AGTGGTGGCC TAACTACGGC TACACTAGAA GGACAGTATT
3540

TGGTATCTGC GCTCTGCTGA AGCCAGTTAC CTTCGGAAAA AGAGTTGGTA GCTCTTGATC
3600

CGGCAAACAA ACCACCGCTG GTAGCGGTGG TTTTTTTGTT TGCAAGCAGC AGATTACGCG
3660

CAGAAAAAAA GGATCTCAAG AAGATCCTTT GATCTTTTCT ACGGGGTCTG ACGCTCAGTG
3720

GAACGAAAAC TCACGTTAAG GGATTTTGGT CATGAGATTA TCAAAAAGGA TCTTCACCTA
3780

GATCCTTTTA AATTAAAAAT GAAGTTTTAA ATCAATCTAA AGTATATATG AGTAAACTTG
3840

GTCTGACAGT TACCAATGCT TAATCAGTGA GGCACCTATC TCAGCGATCT GTCTATTTCG
3900

TTCATCCATA GTTGCCTGAC TCCCCGTCGT GTAGATAACT ACGATACGGG AGGGCTTACC
3960

ATCTGGCCCC AGTGCTGCAA TGATACCGCG AGACCCACGC TCACCGGCTC CAGATTTATC
4020

AGCAATAAAC CAGCCAGCCG GAAGGGCCGA GCGCAGAAGT GGTCCTGCAA CTTTATCCGC
4080

CTCCATCCAG TCTATTAATT GTTGCCGGGA AGCTAGAGTA AGTAGTTCGC CAGTTAATAG
4140

TTTGCGCAAC GTTGTTGCCA TTGCTACAGG CATCGTGGTG TCACGCTCGT CGTTTGGTAT
4200

GGCTTCATTC AGCTCCGGTT CCCAACGATC AAGGCGAGTT ACATGATCCC CCATGTTGTG
4260

CAAAAAGCG GTTAGCTCCT TCGGTCCTCC GATCGTTGTC AGAAGTAAGT TGGCCGCAGT
4320

FIGURE 8E

```
GTTATCACTC ATGGTTATGG CAGCACTGCA TAATTCTCTT ACTGTCATGC CATCCGTAAG
                                                                4380

ATGCTTTTCT GTGACTGGTG AGTACTCAAC CAAGTCATTC TGAGAATAGT GTATGCGGCG
                                                                4440

ACCGAGTTGC TCTTGCCCGG CGTCAATACG GGATAATACC GCGCCACATA GCAGAACTTT
                                                                4500

AAAAGTGCTC ATCATTGGAA AACGTTCTTC GGGGCGAAAA CTCTCAAGGA TCTTACCGCT
                                                                4560

GTTGAGATCC AGTTCGATGT AACCCACTCG TGCACCCAAC TGATCTTCAG CATCTTTTAC
                                                                4620

TTTCACCAGC GTTTCTGGGT GAGCAAAAAC AGGAAGGCAA AATGCCGCAA AAAAGGGAAT
                                                                4680

AAGGGCGACA CGGAAATGTT GAATACTCAT ACTCTTCCTT TTTCAATATT ATTGAAGCAT
                                                                4740

TTATCAGGGT TATTGTCTCA TGAGCGGATA CATATTTGAA TGTATTTAGA AAAATAAACA
                                                                4800

AATAGGGGTT CCGCGCACAT TTCCCCGAAA AGTGCCACCT GACGTCTAAG AAACCATTAT
                                                                4860

TATCATGACA TTAACCTATA AAAATAGGCG TATCACGAGG CCCTTTCGTC
                                                      4910
```

HYBRID ADENOVIRUS-AAV VECTOR AND METHODS OF USE THEREFOR

This invention was supported by the National Institute of Health Grant No. P30 DK 47757. The United States government has rights in this invention.

FIELD OF THE INVENTION

The present invention relates to the field of vectors useful in somatic gene therapy and the production thereof.

BACKGROUND OF THE INVENTION

Human gene therapy is an approach to treating human disease that is based on the modification of gene expression in cells of the patient. It has become apparent over the last decade that the single most outstanding barrier to the success of gene therapy as a strategy for treating inherited diseases, cancer, and other genetic dysfunctions is the development of useful gene transfer vehicles. For optimal use, gene transfer vehicles must have the following characteristics: (1) the ability to transduce a selected gene into a nondividing cell efficiently; (2) the ability to transduce with specificity into a wide variety of target cells; (3) the ability to provide transient or long-term, stable transgene expression; and (4) the ability to present no health risk to the recipient. It is equally important from a practical/technical standpoint that the envisioned vectors are easy to manipulate and manufacture.

Eukaryotic viruses have been employed as vehicles for somatic gene therapy. Among the viral vectors that have been cited frequently in gene therapy research are adenovirus and adeno-associated virus (AAV). Adenovirus and AAV are eukaryotic DNA viruses that can be modified to efficiently deliver a therapeutic or reporter transgene to a variety of cell types. These viral vectors, however, also have inherent limitations in use as vehicles for somatic gene therapy.

Adenovirus vectors are capable of providing extremely high levels of transgene delivery to virtually all cell types, regardless of the mitotic state. High titers ($10^{13}$ plaque forming units/ml) of recombinant virus can be easily generated in 293 cells (the adenovirus equivalent to retrovirus packaging cell lines) and cryostored for extended periods without appreciable losses. The efficacy of this system in delivering a therapeutic transgene in vivo that complements a genetic imbalance has been demonstrated in animal models of various disorders [Y. Watanabe, *Atherosclerosis*, 36:261–268 (1986); K. Tanzawa et al, *FEBS Letters*, 118(1):81–84 (1980); J. L. Golasten et al, *New Engl. J. Med.*, 309(11983):288–296 (1983); S. Ishibashi et al, *J. Clin. Invest.*, 92:883–893 (1993); and S. Ishibashi et al, *J. Clin. Invest.*, 93:1885–1893 (1994)]. Indeed, recombinant replication defective adenovirus encoding a cDNA for the cystic fibrosis transmembrane regulator (CFTR) has been approved for use in at least two human CF clinical trials [see, e.g., J. Wilson, *Nature*, 365:691–692 (Oct. 21, 1993)].

The primary limitation of this virus as a vector resides in the complexity of the adenovirus genome. A human adenovirus is comprised of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis [see, e.g., Horwitz, *Virology*, 2d edit., ed. B. N. Fields, Raven Press, Ltd. New York (1990)].

A human adenovirus undergoes a highly regulated program during its normal viral life cycle [Y. Yang et al, *Proc. Natl. Acad. Sci. USA*, 91:4407–4411 (1994)]. Virions are internalized by receptor-mediated endocytosis and transported to the nucleus where the immediate early genes, E1a and E1b, are expressed. Because these early gene products regulate expression of a variety of host genes (which prime the cell for virus production) and are central to the cascade activation of early delayed genes (e.g. E2, E3, and E4) followed by late genes (e.g. L1–5), first generation adenovirus vectors for gene therapy focused on the removal of the E1 domain. This strategy was successful in rendering the vectors replication defective, however, in vivo studies revealed transgene expression was transient and invariably associated with the development of severe inflammation at the site of vector targeting [S. Ishibashi et al, *J. Clin. Invest.*, 93:1885–1893 (1994); J. M. Wilson et al, *Proc. Natl. Acad. Sci., USA*, 85:4421–4424 (1988); J. M. Wilson et al, *Clin. Bio.*, 3:21–26 (1991); M. Grossman et al, *Som. Cell. and Mol. Gen.*, 17:601–607 (1991)].

Adeno-associated viruses (AAV) have also been employed as vectors for somatic gene therapy. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene [B. J. Carter, in "Handbook of Parvoviruses", ed., P. Tijsser, CRC Press, pp.155–168 (1990)]. It has been shown that the ITRs represent the minimal sequence required for replication, rescue, packaging, and integration of the AAV genome.

The AAV life cycle is biphasic, composed of both latent and lytic episodes. During a latent infection, AAV virions enter a cell as an encapsidated ssDNA, and shortly thereafter are delivered to the nucleus where the AAV DNA stably integrates into a host chromosome without the apparent need for host cell division. In the absence of helper virus, the integrated ss DNA AAV genome remains latent but capable of being activated and rescued. The lytic phase of the life cycle begins when a cell harboring an AAV provirus is challenged with a secondary infection by a herpesvirus or adenovirus which encodes helper functions that are recruited by AAV to aid in its excision from host chromatin [B. J. Carter, cited above]. The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or − ss DNA genomes following cell lysis.

Progress towards establishing AAV as a transducing vector for gene therapy has been slow for a variety of reasons. While the ability of AAV to integrate in quiescent cells is important in terms of long term expression of a potential transducing gene, the tendency of the integrated provirus to preferentially target only specific sites in chromosome 19 reduces its usefulness. Additionally, difficulties surround large-scale production of replication defective recombinants. In contrast to the production of recombinant retrovirus or adenovirus, the only widely recognized means for manufacturing transducing AAV virions entails co-transfection with two different, yet complementing plasmids. One of these contains the therapeutic or reporter minigene sandwiched between the two cis acting AAV ITRs. The AAV components that are needed for rescue and subsequent packaging of progeny recombinant genomes are provided in trans by a second plasmid encoding the viral open reading frames for rep and cap proteins. The cells targeted for transfection must also be infected with adenovirus thus providing the necessary helper functions. Because the yield of recombinant AAV is dependent on the number of cells that are transfected with the cis and trans-acting plasmids, it is desirable to use a transfection protocol with high efficiency. For large-scale production of high titer virus, however, previously employed high efficiency calcium phosphate and liposome systems are cumbersome and subject to inconsistencies.

There remains a need in the art for the development of vectors for gene therapy which overcome the disadvantages of the known vector systems.

SUMMARY OF THE INVENTION

In one aspect, the present invention provides a unique hybrid adenovirus/AAV viral particle, which comprises an adenovirus capsid containing selected portions of an adenovirus sequence, 5' and 3' AAV ITR sequences which flank a selected transgene under the control of a selected promoter and other conventional vector regulatory components. This hybrid viral particle is characterized by high titer transgene delivery to a host cell and the ability to stably integrate the transgene into the host cell chromosome. In one embodiment, the transgene is a reporter gene. Another embodiment of the hybrid viral particle contains a therapeutic transgene. Still another embodiment of the hybrid vector particle has associated therewith a polycation sequence. Another embodiment of the hybrid viral particle also includes an AAV rep gene.

In another aspect, the present invention provides a hybrid vector construct for use in producing the viral particle described above. This hybrid vector comprises selected portions of an adenovirus sequence, 5' and 3' AAV ITR sequences which flank a selected transgene under the control of a selected promoter and other conventional vector regulatory components. Another embodiment of the hybrid viral particle also includes an AAV rep gene.

In another aspect, the invention provides a method for delivering a selected gene to a host cell for expression in that cell by employing the hybrid viral particle of this invention. Such a method may be employed to deliver a therapeutic gene to a targeted host cell to treat or correct a genetically associated disorder or disease.

In yet another aspect, the present invention provides a method for producing the hybrid viral particle by transfecting a suitable packaging cell line with the hybrid construct of this invention. In another embodiment the method involves co-transfecting a cell line (either a packaging cell line or a non-packaging cell line) with a hybrid construct and a suitable helper adenovirus.

In a further aspect, the present invention provides a method for producing large quantities of recombinant AAV particles with high efficiency by employing the above methods, employing the hybrid construct of this invention and collecting the rAAV particles from a cell line transfected with the vector.

Other aspects and advantages of the present invention are described further in the following detailed description of the preferred embodiments thereof.

BRIEF DESCRIPTION OF THE DRAWINGS

FIG. 1A is a schematic diagram of a vector construct pAd.AV.CMVLacZ [SEQ ID NO: 1], which contains (from the top in clockwise order) adenovirus sequence map units 0–1 (clear bar), the 5' AAV ITR (solid bar); a CMV immediate early enhancer/promoter (hatched arrow), an SV40 intron (clear bar), an E. coli beta-galactosidase cDNA (LacZ) (hatched line), an SV40 polyadenylation signal (clear bar), a 3' AAV ITR (solid bar), adenovirus sequence from map units 9–16 (clear bar), and a portion of a pBR322 derivative plasmid (thin solid line). Restriction endonuclease enzymes are identified by their conventional designations; and the location of each restriction enzyme is identification by the nucleotide number in parentheses to the right of the enzyme designation.

FIG. 1B is a schematic drawing demonstrating linearization of pAd.AV.CMVLacZ [SEQ ID NO: 1] by digestion with restriction enzyme NheI and a linear arrangement of a ClaI digested adenovirus type 5 with deletions from mu 0–1. The area where homologous recombination will occur (between m.u. 9–16) in both the plasmid and adenovirus sequences is indicated by crossed lines.

FIG. 1C is a schematic drawing which demonstrates the hybrid vector Ad.AV.CMVLacZ after co-transfection of the linearized pAd.AV.CMVLacZ [SEQ ID NO: 1] and adenovirus into 293 cells followed by intracellular homologous recombination.

FIGS. 2A–2J reports the top DNA strand of the double-strand plasmid pAd.AV.CMVLacZ [SEQ ID NO: 1] (the complementary strand can be readily derived by one of skill in the art). Nucleotides 1–365 of SEQ ID NO: 1 and 5221 to 10,398 of SEQ ID NO: 1 are adenovirus type 5 sequences; the 5' AAV ITR sequence spans nucleotides 365–538 of SEQ ID NO: 1; the CMV promoter/enhancer spans nucleotides 563–1157 of SEQ ID NO: 1; the SV-40 intron spans nucleotides 1158–1179 of SEQ ID NO: 1; the LacZ gene spans nucleotides 1356–4827 of SEQ ID NO: 1; the SV-40 poly A sequence spans nucleotides 4839–5037 of SEQ ID NO: 1; the 3' AAV ITR spans nucleotides 5053 to 5221 of SEQ ID NO: 1. All remaining sequences is nonspecific/plasmid linker sequence.

FIGS. 8A–8E reports the top DNA strand of the double-strand plasmid pRep78/52 [SEQ ID NO: 2] (the complementary strand can be readily derived by one of skill in the art).

DETAILED DESCRIPTION OF THE INVENTION

Figure 3:
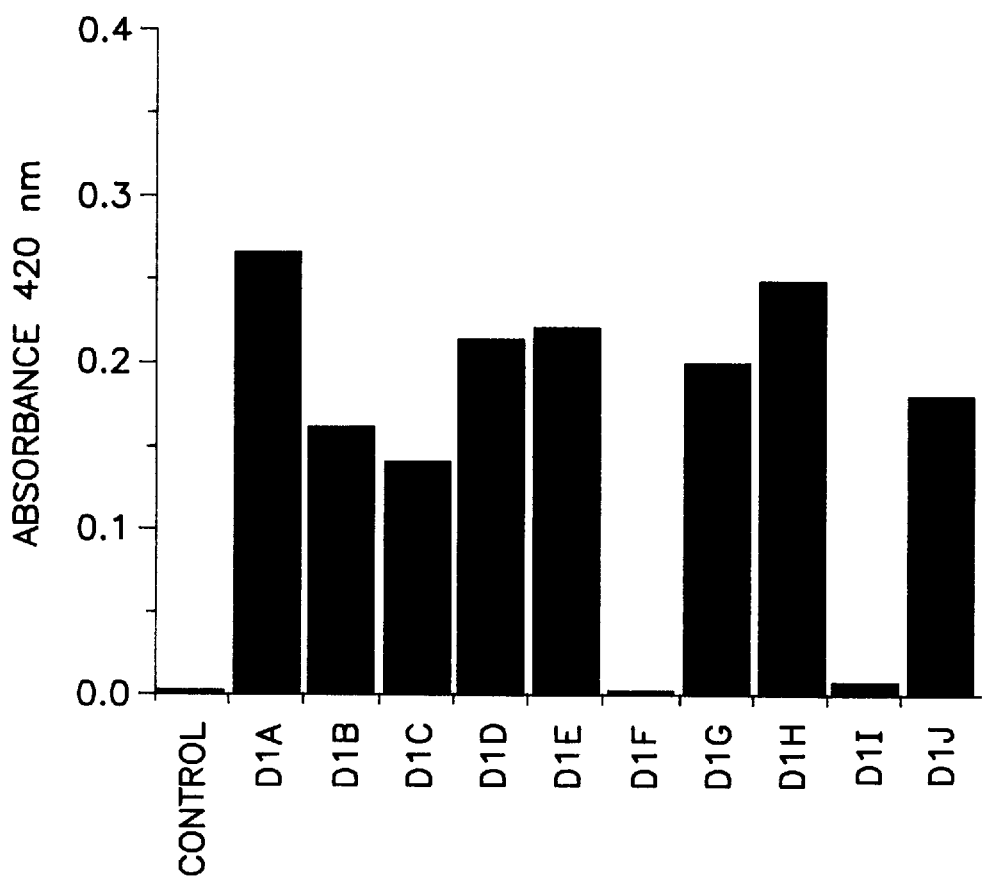
FIG. 3 is a bar graph plotting u.v. absorbance at 420 nm of the beta-galactosidase blue color for a control and ten putative positive clones (D1A through D1J) of 293 cells transfected with the recombinant hybrid Ad.AV.CMVLacZ. Eight of the clones expressed high levels of enzyme.

The present invention provides a unique gene transfer vehicle which overcomes many of the limitations of prior art vectors. This engineered hybrid virus contains selected adenovirus domains and selected AAV domains as well as a selected transgene and regulatory elements in a viral capsid. This novel hybrid virus vector solves the problems observed with other, conventional gene therapy viral vectors, because it is characterized by the ability to provide extremely high levels of transgene delivery to virtually all cell types (conferred by its adenovirus sequence) and the ability to provide stable long-term transgene integration into the host cell (conferred by its AAV sequences). The adenovirus-AAV hybrid virus of this invention has utility both as a novel gene transfer vehicle and as a reagent in a method for large-scale recombinant AAV production.

I. Construction of the Hybrid Vector

A. The Adenovirus Component of the Vector

The hybrid vector of this invention uses adenovirus nucleic acid sequences as a shuttle to deliver a recombinant AAV/transgene genome to a target cell. The DNA sequences of a number of adenovirus types, including type Ad5, are available from Genbank. The adenovirus sequences may be obtained from any known adenovirus type, including the presently identified 41 human types [Horwitz et al, cited above]. Similarly adenoviruses known to infect other animals may also be employed in the vector constructs of this invention. The selection of the adenovirus type is not anticipated to limit the following invention. A variety of adenovirus strains are available from the American Type Culture Collection, Rockville, Md., or available by request from a variety of commercial and institutional sources. In the following exemplary embodiment an adenovirus, type 5 (Ad5) is used for convenience.

The adenovirus nucleic acid sequences employed in the hybrid vector of this invention can range from a minimum sequence amount, which requires the use of a helper virus to produce the hybrid virus particle, to only selected deletions of adenovirus genes, which deleted gene products can be supplied in the hybrid viral production process by a selected packaging cell. Specifically, at a minimum, the adenovirus nucleic acid sequences employed in the pAdΔ shuttle vector of this invention are adenovirus genomic sequences from which all viral genes are deleted which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. According to this invention, the entire adenovirus 5' sequence containing the 5'ITR and packaging/enhancer region can be employed as the 5' adenovirus sequence in the hybrid vector. This left terminal (5') sequence of the Ad5 genome useful in this invention spans bp 1 to about 360 of the conventional adenovirus genome, also referred to as map units 0–1 of the viral genome, and generally is from about 353 to about 360 nucleotides in length. This sequence includes the 5'ITR (bp 1–103 of the adenovirus genome); and the packaging/enhancer domain (bp 194–358 of the adenovirus genome). Preferably, this native adenovirus 5' region is employed in the hybrid vector in unmodified form.

The 3' adenovirus sequences of the hybrid vector include the right terminal (3') ITR sequence of the adenoviral genome spanning about bp 35,353—end of the adenovirus genome, or map units ~98.4–100. This sequence is generally about 580 nucleotide in length. This entire sequence is desirably employed as the 3' sequence of a hybrid vector. Preferably, the native adenovirus 3' region is employed in the hybrid vector in unmodified form. However, some modifications to these sequences which do not adversely effect their biological function may be acceptable. As described below, when these adenovirus sequences are employed in the hybrid vector, a helper adenovirus which supplies all other essential genes for viral formation alone or with a packaging cell line is required in the production of the viral vector.

Alternative embodiments of the hybrid vector employ adenovirus sequences in addition to the minimum sequences, but which contain deletions of all or portions of adenovirus genes. For example, the adenovirus immediate early gene E1a (which spans mu 1.3 to 4.5) and delayed early gene E1b (which spans mu 4.6 to 11.2) should be deleted from the adenovirus sequence which forms a part of the hybrid construct. Alternatively, if these sequences are not completely eliminated, at least a sufficient portion of the E1a and E1b sequences must be deleted so as to eliminate their biological function.

Additionally, all or a portion of the adenovirus delayed early gene E3 (which spans mu 76.6 to 86.2) may be eliminated from the adenovirus sequence which forms a part of the hybrid construct. The function of E3 is irrelevant to the function and production of the hybrid virus particle.

All or a portion of the adenovirus delayed early gene E2a (which spans mu 67.9 to 61.5) may be eliminated from the adenovirus which forms a part of the hybrid construct. It is also anticipated that portions of the other delayed early genes E2b (which spans mu 29 to 14.2) and E4 (which spans mu 96.8 to 91.3) may also be eliminated from the adenovirus portion of the vector.

Deletions may also be made in any of the late genes L1 through L5, which span mu 16.45 to 99 of the adenovirus genome. Similarly, deletions may be useful in the intermediate genes IX which maps between mu 9.8 and 11.2 and IVa$_2$ which maps between 16.1 to 11.1. Other deletions may occur in the other structural or non-structural adenovirus.

The above discussed deletions may occur individually, i.e., an adenovirus sequence for use in the present invention may contain deletions of E1 only. Alternatively, deletions of entire genes or portions effective to destroy their biological activity may occur in any combination. For example, in one exemplary hybrid vector, the adenovirus sequence may contain deletions of the E1 genes and the E3 gene, or of the E1, E2a and E3 genes, or of the E1 and E4 genes, or of E1, E2a and E4 genes, with or without deletion of E3, and so on.

The more deletions in the adenovirus sequence up to the minimum sequences identified above that characterize the hybrid vector, the larger the sequence(s) of the other below-described components to be inserted in the hybrid vector. As described above for the minimum adenovirus sequences, those gene sequences not present in the adenovirus portion of the hybrid vector must be supplied by either a packaging cell line and/or a helper adenovirus to generate the hybrid viral particle.

In an exemplary hybrid vector of this invention which is described below and in Example 1, the adenovirus genomic sequences present are from mu 0 to 1, mu 9 to 78.3 and mu 86 to 100 (deleted sequences eliminate the E1a and E1b genes and a portion of the E3 gene). From the foregoing information, it is expected that one of skill in the art may construct hybrid vectors containing more or less of the adenovirus gene sequence.

The portions of the adenovirus genome in the hybrid vector permit high production titers of the vector to be produced, often greater than $1 \times 10^{13}$ pfu/ml. This is in stark contrast to the low titers ($1 \times 10^6$ pfu/ml) that have been found for recombinant AAV.

B. The AAV Components of the Vector

Also part of the hybrid vectors of this invention are sequences of an adeno-associated virus. The AAV sequences useful in the hybrid vector are the viral sequences from which the rep and cap polypeptide encoding sequences are deleted. More specifically, the AAV sequences employed are the cis-acting 5' and 3' inverted terminal repeat (ITR) sequences [See, e.g., B. J. Carter, in "Handbook of Parvoviruses", ed., P. Tijsser, CRC Press, pp.155–168 (1990). As stated above, the ITR sequences are about 143 bp in length. Substantially the entire sequences encoding the ITRs are used in the vectors, although some degree of minor modification of these sequences is expected to be permissible for this use. The ability to modify these ITR sequences is within the skill of the art. See, e.g., texts such as Sambrook et al, "Molecular Cloning. A Laboratory Manual.", 2d edit., Cold Spring Harbor Laboratory, New York (1989).

The AAV ITR sequences may be obtained from any known AAV, including presently identified human AAV types. Similarly, AAVs known to infect other animals may also be employed in the vector constructs of this invention. The selection of the AAV is not anticipated to limit the following invention. A variety of AAV strains, types 1–4, are available from the American Type Culture Collection or available by request from a variety of commercial and institutional sources. In the following exemplary embodiment an AAV-2 is used for convenience.

In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus, i.e., after map unit 1. Alternatively, the AAV sequences may be inserted at an E3 deletion, E2a deletion, and so on. If only the adenovirus 5' ITR/packaging sequences and 3' ITR sequences are used in the vector, the AAV sequences are inserted between them.

C. The Transgene Component of the Vectors

The transgene sequence of the vector is a nucleic acid sequence or reverse transcript thereof, heterologous to the adenovirus sequence, which encodes a polypeptide or protein of interest. The transgene is operatively linked to regulatory components in a manner which permits transgene transcription.

The composition of the transgene sequence will depend upon the use to which the resulting hybrid vector will be put. For example, one type of transgene sequence includes a reporter sequence, which upon expression produces a detectable signal. Such reporter sequences include without limitation an *E. coli* beta-galactosidase (LacZ) cDNA, an alkaline phosphatase gene and a green fluorescent protein gene. These sequences, when associated with regulatory elements which drive their expression, provide signals detectable by conventional means, e.g., ultraviolet wavelength absorbance, visible color change, etc.

Another type of transgene sequence includes a therapeutic gene which expresses a desired gene product in a host cell. These therapeutic nucleic acid sequences typically encode products for administration and expression in a patient in vivo or ex vivo to replace or correct an inherited or non-inherited genetic defect or treat an epigenetic disorder or disease. Such therapeutic genes which are desirable for the performance of gene therapy include, without limitation, a normal cystic fibrosis transmembrane regulator (CFTR) gene, a low density lipoprotein (LDL) gene, and a number of genes which may be readily selected by one of skill in the art. The selection of the transgene is not considered to be a limitation of this invention, as such selection is within the knowledge of the art-skilled.

D. Regulatory Elements of the Hybrid Vector

In addition to the major elements identified above for the hybrid vector, i.e., the adenovirus sequences, AAV sequences and the transgene, the vector also includes conventional regulatory elements necessary to drive expression of the transgene in a cell transfected with the hybrid vector. Thus the vector contains a selected promoter which is linked to the transgene and located, with the transgene, between the AAV ITR sequences of the vector.

Selection of the promoter is a routine matter and is not a limitation of the hybrid vector itself. Useful promoters may be constitutive promoters or regulated (inducible) promoters, which will enable control of the amount of the transgene to be expressed. For example, a desirable promoter is that of the cytomegalovirus immediate early promoter/enhancer [see, e.g., Boshart et al, *Cell,* 41:521–530 (1985)]. Another desirable promoter includes, without limitation, the Rous sarcoma virus LTR promoter/enhancer. Still other promoter/enhancer sequences may be selected by one of skill in the art.

The vectors will also desirably contain nucleic acid sequences heterologous to the adenovirus sequences including sequences providing signals required for efficient polyadenylation of the transcript and introns with functional splice donor and acceptor sites. A common poly-A sequence which is employed in the exemplary vectors of this invention is that derived from the papovavirus SV-40. The poly-A sequence generally is inserted in the vector following the transgene sequences and before the 3' AAV ITR sequence. A common intron sequence is also derived from SV-40, and is referred to as the SV-40 T intron sequence. A hybrid vector of the present invention may also contain such an intron, desirably located between the promoter/enhancer sequence and the transgene. Selection of these and other common vector elements are conventional and many such sequences are available [see, e.g., Sambrook et al, and references cited therein]. The DNA sequences encoding such regulatory regions are provided in the plasmid sequence of FIG. 2 [SEQ ID NO: 1].

The combination of the transgene, promoter/enhancer, the other regulatory vector elements and the flanking 5' and 3' AAV ITRs are referred to as a "minigene" for ease of reference herein. As above stated, the minigene is located in the site of any selected adenovirus deletion in the vector. The size of this minigene depends upon the amount and number of adenovirus sequence deletions referred to above. Such a minigene may be about 8 kb in size in the exemplary vector deleted in the E1 and E3 genes, as described in the examples below. Alternatively, if only the minimum adenovirus sequences are employed in the vector, this minigene may be a size up to about 30 kb. Thus, this hybrid vector permits a great deal of latitude in the selection of the various components of the minigene, particularly the transgene, with regard to size. Provided with the teachings of this invention, the design of such a minigene can be made by resort to conventional techniques.

E. Hybrid Vector Assembly and Production of Hybrid Viral Particle

The material from which the sequences used in the hybrid vector, helper viruses, if needed, and viral particle are derived and the various vector components and sequences employed in the construction of the hybrid vectors of this invention are obtained from commercial or academic sources based on previously published and described materials. These materials may also be obtained from an individual patient or generated and selected using standard recombinant molecular cloning techniques known and practiced by those skilled in the art. Any modification of existing nucleic acid sequences forming the vectors, including sequence deletions, insertions, and other mutations are also generated using standard techniques.

Assembly of the selected DNA sequences of the adenovirus, the AAV and the reporter genes or therapeutic genes and other vector elements into the hybrid vector and the use of the hybrid vector to produce a hybrid viral particle utilize conventional techniques, such as described in Example 1. Such techniques include conventional cloning techniques of cDNA such as those described in texts [Sambrook et al, cited above], use of overlapping oligonucleotide sequences of the adenovirus and AAV genomes, polymerase chain reaction, and any suitable method which provides the desired nucleotide sequence. Standard transfection and co-transfection techniques are employed, e.g., CaPO$_4$ transfection techniques using the complementation human embryonic kidney (HEK) 293 cell line (a human kidney cell line containing a functional adenovirus E1a gene which provides a transacting E1a protein). Other conventional methods employed in this invention include homologous recombination of the viral genomes, plaquing of viruses in agar overlay, methods of measuring signal generation, and the like.

As described in detail in Example 1 below and with resort to FIG. 1, a unique hybrid vector of this invention is prepared which contains an E1-deleted, partially E3 deleted, adenovirus sequence associated with a single copy of a recombinant AAV having deletions of its rep and cap genes and encoding a selected reporter transgene. Briefly, this exemplary hybrid vector was designed such that the AV.C-MVLacZ sequence [SEQ ID NO: 1] (a minigene containing a 5'AAV ITR, a CMV promoter, an SV-40 intron, a LacZ transgene, an SV-40 poly-A sequence and a 3'AAV ITR) was positioned in place of the adenovirus type 5 (Ad5) E1a/E1b genes, making the adenovirus vector replication defective (see, the circular hybrid vector of FIG. 1A.

Because of the limited amount of adenovirus sequence present in the hybrid vectors of this invention, including the pAV.CMVLacZ [SEQ ID NO: 1] above, packaging cell line or a helper adenovirus or both may be necessary to provide sufficient adenovirus gene sequences necessary for a productive viral infection to generate the hybrid virus particle.

Helper viruses useful in this invention contain selected adenovirus gene sequences not present in the hybrid vector construct or expressed by the cell line in which the hybrid vector is transfected, and may optionally contain a second reporter minigene. This second reporter is used to enable separation between the resulting hybrid virus and the helper virus upon purification. The construction of desirable helper cells is within the skill of the art.

As one example, if the cell line employed to produce the viral vector is not a packaging cell line, and the hybrid vector contains only the minimum adenovirus sequences identified above, the helper virus may be a wild type Ad vector. Thus, the helper virus supplies the necessary adenovirus early genes E1, E2a , E4 and all remaining late, intermediate, structural and non-structural genes of the adenovirus genome. However, if, in this situation, the packaging cell line is 293, which supplies the E1 proteins, the helper cell line need not contain the E1 gene.

In another embodiment, if the hybrid construct is replication defective (no E1 gene and optionally no E3 gene) and the 293 cell line is employed, no helper virus is necessary for production of the hybrid virus.

Additionally, all or a portion of the adenovirus delayed early gene E3 (which spans mu 76.6 to 86.2) may be eliminated from the helper virus useful in this invention because this gene product is not necessary for the formation of a functioning hybrid virus particle.

It should be noted that one of skill in the art may design other helper viruses or develop other packaging cell lines to complement the adenovirus deletions in the vector construct and enable production of the hybrid virus particle, given this information. Therefore, this invention is not limited by the use or description of any particular helper virus or packaging cell line.

Thus, as described in FIGS. 1A through 1C, the circular plasmid pAd.AV.CMVLacZ [SEQ ID NO: 1] (containing the minigene and only adenovirus sequences from map unit 0 to 1 and 9 to 16) was digested and co-transfected with a selected Ad5 helper virus (containing adenovirus sequences 9 to 78.4 and 86 to 100) into 293 cells. Thus, the packaging cell line provides the E1 proteins and the helper virus provides all necessary adenovirus gene sequences subsequent to map unit 16. Homologous recombination occurs between the helper and the vector, resulting in the hybrid vector/viral particle. Growth of this hybrid viral particle in 293 cells has been closely monitored for greater than 20 rounds of amplification with no indication of genome instability. Rescue and integration of the transgene from the hybrid virus into a host cell and further modifications of the vector are described below. The resulting hybrid viral particle Ad.AV.CMVLacZ combines the high titer potential of adenovirus with the integrating biology associated with AAV latency.

G. Hybrid Vector Polycation Conjugates

The hybrid vector/viruses described above may be further modified by resort to adenovirus-polylysine conjugate technology. See, e.g., Wu et al, *J. Biol. Chem.*, 264:16985–16987 (1989); and K. J. Fisher and J. M. Wilson, *Biochem. J.*, 299: 49 (Apr. 1, 1994), incorporated herein by reference. Using this technology, a hybrid virus as described above is modified by the addition of a poly-cation sequence distributed around the capsid of the hybrid viral particle. Preferably, the poly-cation is poly-lysine, which attaches around the negatively-charged virus to form an external positive charge. A plasmid containing the AAV rep gene under the control of a suitable promoter is then complexed directly to the hybrid capsid, resulting in a single viral particle containing the hybrid virus and an AAV rep gene. Essentially the techniques employed in constructing this embodiment of the hybrid virus vector are as described in detail in Example 3 below.

An alternative embodiment of the hybrid vector and resulting hybrid virus is provided by altering the rep containing plasmid to also contain an AAV cap gene. This embodiment of the hybrid vector when in a host cell is thus able to produce a recombinant AAV particle, as discussed in more detail below.

The plasmids employed in these embodiments contain conventional plasmid sequences, which place a selected AAV sequence, i.e., rep and/or cap gene sequences, under the control of a selected promoter. In the example provided below, the exemplary plasmid is pRep78/52 [SEQ ID NO: 2], a trans-acting plasmid containing the AAV sequences that encode rep 78 kD and 52 kD proteins under the control of the AAV P5 promoter. The plasmid also contains an SV40 polyadenylation signal. The DNA sequence of this plasmid is provided in FIG. 8 [SEQ ID NO: 2].

In a similar manner and with resort to plasmid and vector sequences known to the art, analogous plasmids may be designed using both rep and cap genes, and different constitutive or regulated promoters, optional poly-A sequences and introns.

The availability of materials to make these modified hybrid vectors and viruses and the AAV rep and/or cap containing vectors and the techniques involved in the assembly of the hybrid vector and rep and/or cap containing plasmids are conventional as described above. The assembly techniques for this hybrid virus conjugate employ the techniques described above for the hybrid vector and the techniques of Wu et al and Fisher et al, cited above. The use of this modified hybrid vector including rescue and integration of the transgene into the host cell is described below.

II. Function of the Hybrid Vector/Viral Particle

A. The Hybrid Vector Infects a Target Cell

Once the hybrid virus or hybrid virus conjugate is constructed as discussed above, it is targeted to, and taken up by, a selected target cell. The selection of the target cell also depends upon the use of the hybrid vector, i.e., whether or not the transgene is to be replicated in vitro for production of a recombinant AAV particle, or ex vivo for production into a desired cell type for redelivery into a patient, or in vivo for delivery to a particular cell type or tissue. Target cells may therefor be any mammalian cell (preferably a human cell). For example, in in vivo use, the vector can target to any cell type normally infected by adenovirus, depending upon the route of administration, i.e., it can target, without limitation, neurons, hepatocytes, epithelial cells and the like. Uptake of the hybrid virus by the cell is caused by the infective ability contributed to the vector by the adenovirus and AAV sequences.

B. The Transgene is Rescued

Once the virus or virus conjugate is taken up by a cell, the AAV ITR flanked transgene must be rescued from the parental adenovirus backbone. Rescue of the transgene is dependent upon supplying the infected cell with an AAV rep gene. Thus, efficacy of the hybrid virus can be measured in terms of rep mediated rescue of AAV from the parental adenovirus template.

The rep genes can be supplied to the virus by several methods. One embodiment for providing rep proteins in trans was demonstrated with the exemplary hybrid vector Ad.AV.CMVLacZ by transfecting into the target monolayer of cells previously infected with the hybrid vector, a liposome enveloped plasmid pRep78/52 [SEQ ID NO: 2] containing the genes encoding the AAV rep 78 kDa and 52 kDa proteins under the control of the AAV P5 promoter. Rescue and amplification of a double-stranded AAV monomer and a double-stranded AAV dimer, each containing the LacZ transgene described above, was observed in 293 cells. This is described in detail in Example 2 and FIG. 4.

The production of rep in trans can be modulated by the choice of promoter in the rep containing plasmid. If high levels of rep expression are important early for rescue of the recombinant AAV domain, a heterologous (non-adenovirus, non-AAV) promoter may be employed to drive expression of rep and eliminate the need for E1 proteins. Alternatively, the low levels of rep expression from P5 that occur in the absence of adenovirus E1 proteins may be sufficient to initiate rescue and optimal to drive integration of the recombinant AAV genome in a selected use.

More preferably for in vivo use, the AAV rep gene may also be delivered as part of the hybrid virus. One embodiment of this single particle concept is supplied by the polycation conjugate hybrid virus (see FIG. 10). Infection of this modified virus conjugate is accomplished in the same manner and with regard to the same target cells as identified above. However, the polylysine conjugate of the hybrid virus onto which was directly complexed a plasmid that encoded the rep 78 and 52 proteins, combines all of the functional components into a single particle structure. Thus, the hybrid virus conjugate permits delivery of a single particle to the cell, which is considerably more desirable for therapeutic use. Similar experiments to demonstrate rescue of the transgene from the hybrid conjugate in 293 cells and in HeLa cells are detailed in Example 4 and FIGS. 4A and 4B.

In another embodiment, the hybrid virus is modified by cloning the rep cDNA directly into the adenovirus genome portion of the hybrid vector. Because it is known that even residual levels of rep expression can interfere with replication of adenovirus DNA, such incorporation of rep into the hybrid vector itself is anticipated to requires possible mutation of the rep genes to encode only selected domains, and the use of inducible promoters to regulate rep expression, as well as careful placement of the rep genes into the adenovirus sequences of the hybrid vector.

C. Transgene Integrates into Chromosome

Figure 10:
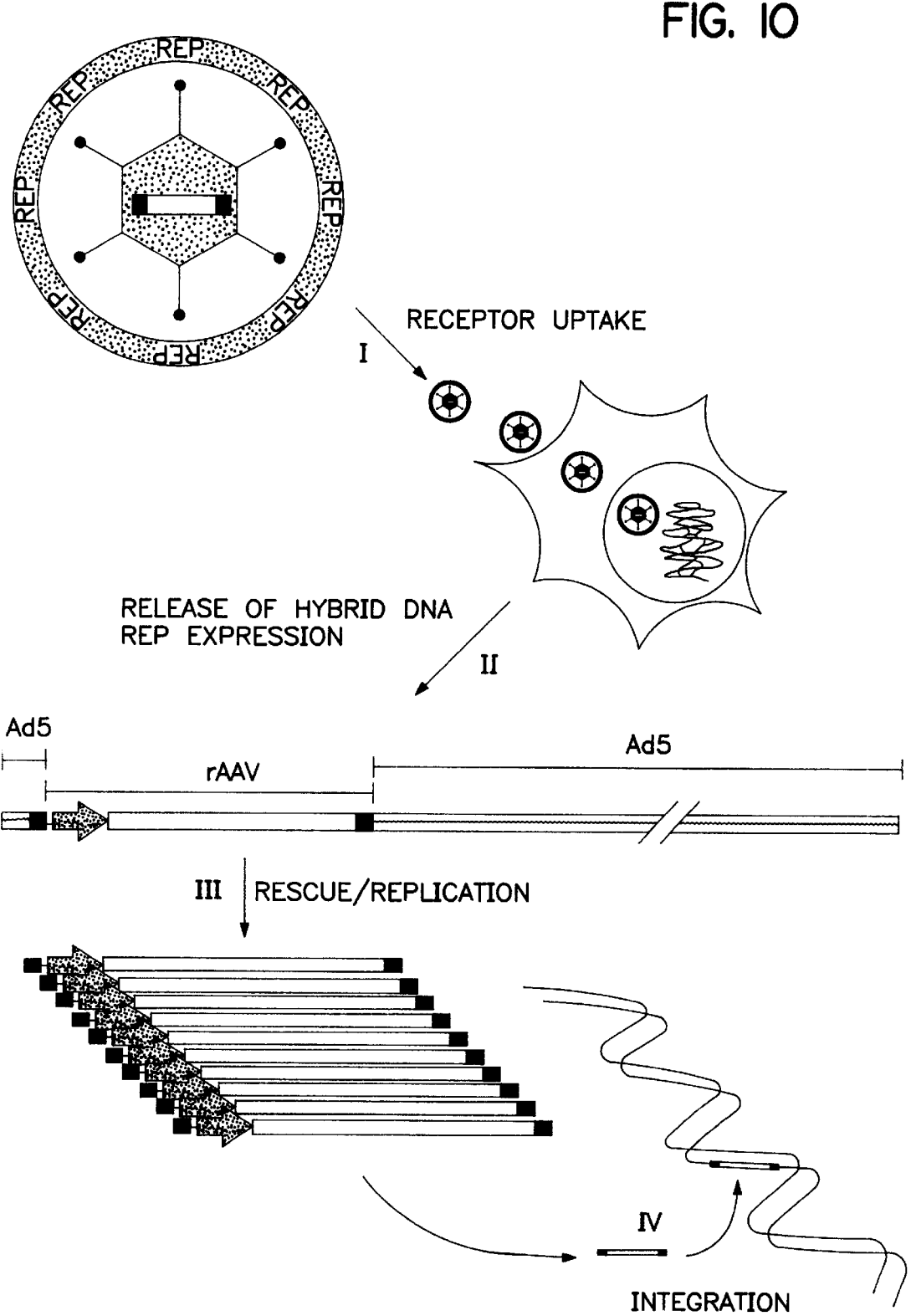
FIG. 10 is a flow diagram of the hybrid vector's life cycle, in which a hybrid conjugate enters the cell and is transported to the nucleus. The virus is uncoated and the rep mediates rescue of the inserted gene, which is then integrated into the chromosome of the host cell.

Once uncoupled (rescued) from the genome of the hybrid virus, the recombinant AAV/transgene minigene seeks an integration site in the host chromatin and becomes integrated therein, providing stable expression of the accompanying transgene in the host cell. This aspect of the function of the hybrid virus is important for its use in gene therapy. The AAV/transgene minigene sequence rescued from the hybrid virus achieves provirus status in the target cell, i.e., the final event in the hybrid lifecycle (FIG. 10).

To determine whether the AAV minigene rescued from the hybrid virus achieves provirus status in a target cell, HeLa cells are infected with the hybrid vector-poly-Lysine conjugate complexed with pRep78/52 [SEQ ID NO: 2] and passaged until stable colonies of LacZ expressing cells are evident. A duplicate plate of cells is infected with the same conjugate, but instead of being complexed with the pRep78/52 plasmid [SEQ ID NO: 2], carries an irrelevant plasmid. Cells that receive the rep containing hybrid particle produce a greater number of stable LacZ positive colonies than cells infected with the control vector. This indicates multiple rescue and integration events in cells that expressed rep proteins. Confirmation of integration is revealed by characterizing the recombinant AAV genome in the hybrid infected cells and identifying flanking chromosomal sequences (see Example 5).

III. Use of the Hybrid Viruses in Gene Therapy

The novel hybrid virus and hybrid virus conjugates of this invention provide efficient gene transfer vehicles for somatic gene therapy. These hybrid viruses are prepared to contain a therapeutic gene in place of the LacZ reporter transgene illustrated in the exemplary vector. By use of the hybrid vectors and viruses containing therapeutic transgenes, these transgenes can be delivered to a patient in vivo or ex vivo to provide for stable integration of the desired gene into a target cell. Thus, these hybrid viruses can be employed to correct genetic deficiencies or defects. Two examples of the generation of gene transfer vehicles for the treatment of cystic fibrosis and familial hypercholesterolemia are described in Examples 6 and 7 below. One of skill in the art can generate any number of other gene transfer vehicles by including a selected transgene for the treatment of other disorders.

The hybrid viruses of the present invention may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The hybrid vectors of this invention may be administered in sufficient amounts to transfect the desired cells and provide sufficient levels of integration and expression of the selected transgene to provide a therapeutic benefit without undue adverse or with medically acceptable physiological effects which can be determined by those skilled in the medical arts. Conventional and pharmaceutically acceptable routes of administration include direct delivery to the target organ, tissue or site, intranasal, intravenous, intramuscular, subcutaneous, intradermal, oral and other parental routes of administration. Routes of administration may be combined, if desired.

Dosages of the hybrid virus will depend primarily on factors such as the condition being treated, the selected gene, the age, weight and health of the patient, and may thus vary among patients. A therapeutically effective human dosage of the hybrid viruses of the present invention is believed to be in the range of from about 20 to about 50 ml of saline solution containing concentrations of from about $1 \times 10^7$ to $1 \times 10^{10}$ pfu/ml hybrid virus of the present invention. A preferred human dosage is about 20 ml saline solution at the above concentrations. The dosage will be adjusted to balance the therapeutic benefit against any side effects. The levels of expression of the selected gene can be monitored to determine the selection, adjustment or frequency of dosage administration.

IV. High Efficiency Production of rAAV

The hybrid vectors and conjugates of this invention have another desirable utility in the production of large quantities of recombinant AAV particles. Due to the complicated current methods for generating AAV, there is only a limited amount of AAV available for use in industrial, medical and academic biotechnology procedures. The vectors of the present invention provide a convenient and efficient method for generating large quantities of rAAV particles.

According to this aspect of the invention, a hybrid vector-poly L-lysine conjugate is constructed as described above and in Example 3 and is employed to produce high levels of rAAV as detailed in Example 8, with the possible modifications described in Example 9 below. Briefly, a plasmid is generated that contains both AAV rep and cap genes under the control of a suitable plasmid and is complexed to the poly-lysine exterior of the hybrid vector as described above. This hybrid vector conjugate is then permitted to infect a selected host cell, such as 293 cells. The presence of both rep and cap permit the formation of AAV particles in the cells and generate an AAV virus titer of about $10^9$ virions. In contrast, current methods involving the transfection of multiple plasmids produce only about $10^7$ virion titer. The rAAV is isolated from the culture by selecting the LacZ-containing blue plaques and purifying them on a cesium chloride gradient.

The benefit of this procedure relates to the fact that the cis AAV element is encoded by the parental adenovirus genome. As a result, the trans plasmid is the only DNA component that is needed for complex formation. The cell is thereby loaded with significantly more copies of the trans-acting rep and cap sequences, resulting in improved efficiency of rescue and packaging.

Numerous comparative studies focusing on the optimal ratio and copy number of the cis and trans plasmids for AAV production indicated that there is a positive correlation between the trans plasmid copy number and yield of recombinant virus. As described in detail in Example 8, the yield of recombinant AV.CMVLacZ virus was increased by 5–10 fold by using the hybrid conjugate instead of a standard adenovirus vector as a poly-cation conjugate substrate.

The primary limitation associated with the production of recombinant AAV using a hybrid virus of this invention relates to difficulties that arise in distinguishing between the two viruses (i.e., adenovirus and AAV) that are produced by the cell. Using the exemplary vectors and vector components of this invention, LacZ histochemical staining could not be used to titer the yield of recombinant AV.CMVLacZ since any contaminating Ad.AV.CMVLacZ hybrid would contribute to the final count. Therefore, a rapid Southern blot technique for quantitating yields of recombinant AAV was incorporated. The assay that was developed enabled not only quantitation and verification of AAV production, but also demonstrated the removal of contaminating hybrid virus from purified AAV stocks.

Another method for detecting contaminating hybrid virions involves modifying the hybrid vector by inserting a small second reporter minigene (i.e., reporter gene, promoter and other expression control sequences, where desired) into the E3 region of the parental adenovirus backbone. Because this reporter is not linked to the AAV domain, contaminating hybrid virus that is present during purification can be monitored by this hybrid-specific marker. Another possible reporter sequence is the nucleic acid sequence for green fluorescent protein. With this hybrid vector containing two reporter sequences, histochemical staining for alkaline phosphatase (adenovirus reporter) or β-galactosidase (AAV reporter) activity can be used to monitor each viral domain.

The following examples illustrate the construction and testing of the hybrid vectors of the present invention and the use thereof in the productions of recombinant AAV. These examples are illustrative only, and do not limit the scope of the present invention.

EXAMPLE 1
Construction of a Hybrid Vector

A first hybrid adenovirus-AAV vector was engineered by homologous recombination between an adenovirus DNA substrate and a complementing plasmid according to protocols previously described [see, e.g., K. F. Kozarsky et al, *J. Biol. Chem.*, 269:13695–13702 (1994) and references cited therein]. The following description refers to the diagram of FIG. 1.

The adenovirus DNA substrate was extracted from CsCl purified dl7001 virions, an Ad5 (serotype subgroup C) variant that carries a 3 kb deletion between mu 78.4 through 86 in the nonessential E3 region (provided by Dr. William Wold, Washington University, St. Louis, Mo.). Viral DNA was prepared for co-transfection by digestion with ClaI (adenovirus genomic bp position 917) which removes the left arm of the genome encompassing adenovirus map units 0–2.5. See lower diagram of FIG. 1B.

The complementing plasmid, pAd.AV.CMVLacZ (see FIG. 1A and FIG. 2 [SEQ ID NO: 1]) was constructed as follows:

A parental cloning vector, pAd.BglII was designed. It contains two segments of wild-type Ad5 genome (i.e., map units 0–1 and 9–16.1) separated by a unique BglII cloning site for insertion of heterologous sequences. The missing Ad5 sequences between the two domains (adenovirus genome bp 361–3327) results in the deletion of E1a and the majority of E1b following recombination with viral DNA.

A recombinant AAV genome (AV.CMVLacZ) was designed and inserted into the BglII site of pAd.BglII to generate the complementing plasmid. The linear arrangement of AV.CMVLacZ [SEQ ID NO: 1] (see top diagram of FIG. 1B) includes:

(a) the 5' AAV ITR (bp 1–173) obtained by PCR using pAV2 [C. A. Laughlin et al, *Gene*, 23: 65–73 (1983)] as template [nucleotide numbers 365–538 of FIG. 2 [SEQ ID NO: 1]];

(b) a CMV immediate early enhancer/promoter [Boshart et al, *Cell,* 41:521–530 (1985); nucleotide numbers 563–1157 of FIG. 2 [SEQ ID NO: 1]], (c) an SV40 intron (nucleotide numbers 1178–1179 of FIG. 2 [SEQ ID NO: 1]), (d) *E. coli* beta-galactosidase cDNA (nucleotide numbers 1356–4827 of FIG. 2 [SEQ ID NO: 1]), (e) an SV40 polyadenylation signal (a 237 Bam HI-BclI restriction fragment containing the cleavage/poly-A signals from both the early and late transcription units; nucleotide numbers 4839–5037 of FIG. 2 [SEQ ID NO: 1]) and (f) 3'AAV ITR, obtained from pAV2 as a SnaBI-BglII fragment (nucleotide numbers 5053–5221 of FIG. 2 [SEQ ID NO: 1]).

The resulting complementing plasmid, pAd.AV.CMV-LacZ (see FIG. 1A and FIG. 2 [SEQ ID NO: 1]), contained a single copy of recombinant AV.CMVLacZ flanked by adenovirus coordinates 0–1 on one side and 9–16.1 on the other. Plasmid DNA was linearized using a unique NheI site immediately 5' to adenovirus map unit zero (0) (resulting in the top diagram of FIG. 1B).

Both the adenovirus substrate and the complementing plasmid DNAs were transfected to 293 cells [ATCC CRL1573] using a standard calcium phosphate transfection procedure [see, e.g., Sambrook et al, cited above]. The end result of homologous recombination involving sequences that map to adenovirus map units 9–16.1 is hybrid Ad.AV.C-MVLacZ (see FIG. 1C) in which the E1a and E1b coding regions from the dl7001 adenovirus substrate are replaced with the AV.CMVLacZ from the plasmid.

Twenty-four hours later, the transfection cocktail was removed and the cells overlayed with 0.8% agarose containing 1× BME and 2% fetal bovine serum (FBS). Once viral plaques developed (typically 10–12 days post-transfection), plaques were initially screened for *E. coli* β-galactosidase (LacZ) activity by overlaying the infected monolayer with agarose supplemented with a histochemical stain for LacZ, according to the procedure described in J. Price et al, *Proc. Natl. Acad. Sci., USA,* 84:156–160 (1987). Positive clones (identified by the deposit of insoluble blue dye) were isolated, subjected to three rounds of freeze (dry ice/ethanol)-thaw (37° C.) and an aliquot of the suspended plaque was used to infect a fresh monolayer of 293 cells seeded on duplicate 60 mm plates.

Twenty-four hours later the cells from one set of plates were fixed and again stained for LacZ activity. Cells from the duplicate plate were harvested, suspended in 0.5 ml 10 mM Tris-Cl, pH8.0, and lysed by performing a series of three freeze (dry ice/ethanol)-thaw (37° C.) cycles. Cell debris was removed by centrifugation and an aliquot of the supernatant used to measure LacZ enzyme activity.

As indicated in FIG. 3, assays for β-galactosidase activity which measured the absorbance at 420 nm of the beta-galactosidase blue color in successful recombinants, revealed that eight of the ten isolated, putative positive clones (D1A through D1J) expressed high levels of enzyme. Histochemical staining produced similar results.

Large-scale production and purification of recombinant virus was performed as described in Kozarsky et al, cited above, and references cited therein.

EXAMPLE 2
Functional Analysis of Hybrid Vector

The ability to rescue the AV.CMVLacZ sequence [SEQ ID NO: 1] from the hybrid vector represented an important feature of the hybrid vector systems of Example 1. To evaluate this feature, it was necessary to provide the necessary AAV gene products in trans that direct AAV excision and amplification (i.e. rep proteins). Furthermore, this experiment was conducted in 293 cells to transcomplement the E1 deletion in the Ad.AV.CMVLacZ clones, because the adenovirus E1 gene proteins have been shown to be important for initiating the lytic phase of the AAV lifecycle.

293 cells were seeded onto 6-well 35 mm plates at a density of 1×10⁶ cells/well. Twenty-four hours later, seeding media [DMEM/10% FBS supplemented with antibiotics] was replaced with 1.0 ml DMEM/2% FBS and infected with Ad.AV.CMVLacZ hybrid clones at an MOI of 1. Two hours later, each well was transfected with 1 µg plasmid pRep78/52 [SEQ ID NO: 2], a trans-acting plasmid that encodes the sequence encoding the AAV rep 78 kD and 52 kD proteins. The rep sequences in this construct are under the control of the AAV P5 promoter and utilize an SV40 polyadenylation signal.

As a positive control for AAV rescue, 293 cells seeded in a 6-well plate as above were co-transfected with a cis-acting AAV plasmid pAV.CMVLacZ and pRep78/52. pAV.CMV-LacZ contained AV.CMVLacZ, the identical sequence encoded by pAd.AV.CMVLacZ [SEQ ID NO: 1] described in Example 1 cloned into the BglII site of pSP72 (Promega).

To provide the necessary adenovirus helper function for AAV rescue, cells were infected with either wild-type Ad5 virus or a first generation E1-deleted virus Ad.CMhpAP at an MOI of 5, approximately 2 hours prior to adding the transfection cocktail. Ad.CMhpAP is identical to Ad.CVM-LacZ (Example 1) with the modification that the alkaline phosphatase sequence (which can be obtained from Genbank) is inserted in place of the LacZ gene.

Transfections were performed with Lipofectamine (BRL) according to the instructions provided by the manufacturer. Thirty hours post-transfection, the cells were harvested and episomal DNA (Hirt extract) prepared as described by J. M. Wilson et al, *J. Biol. Chem.*, 267:(16):11483–11489 (1992). Samples were resolved on a 1.2% agarose gel and electroblotted onto a nylon membrane. Blots were hybridized (Southern) with a P-32 random primer-labeled restriction fragment isolated from the *E. coli* LacZ cDNA.

Figures 4A, 4B:
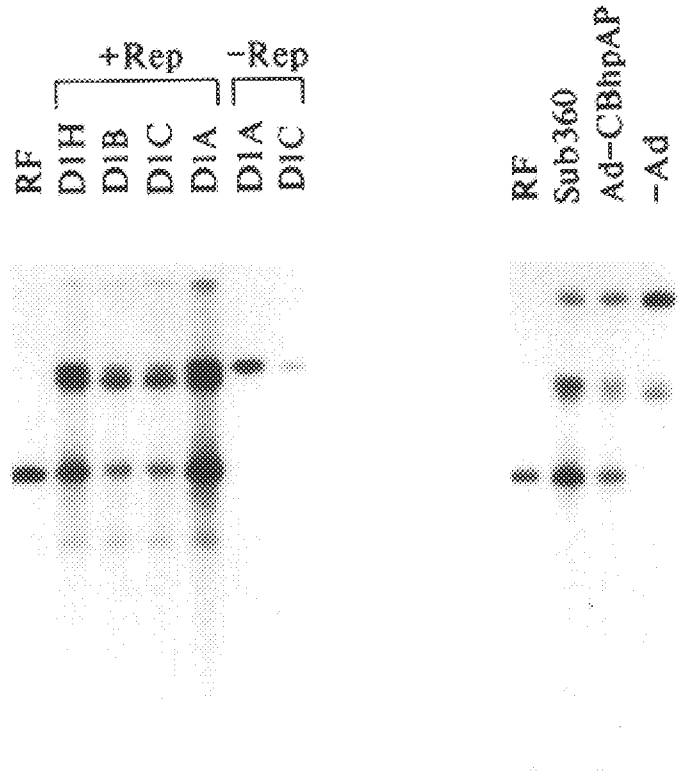
FIG. 4A is an autoradiogram demonstrating rep mediated rescue of the AV.CMVLacZ sequence [SEQ ID NO: 1] from cells transfected with the hybrid Ad.AV.CMVLacZ vectors and a rep containing plasmid. Lane 1 is the replicating form of Ad.AV.CMVLacZ; lanes 2–4 show D1H, D1B, D1C and D1A of Example 1 in the presence of rep; lanes 5 and 6 show D1A and D1C in the absence of rep.
FIG. 4B is an autoradiogram demonstrating rescue of the AV.CMVLacZ sequence [SEQ ID NO: 1] using a conventional cis and trans plasmid-based approach. See, Example 2.

FIG. 4 is an autoradiogram of the resulting blot of rep mediated rescue of the AV.CMVLacZ sequence [SEQ ID NO: 1] from the Ad.AV.CMVLacZ hybrids. Specifically, lane 1 of autoradiogram of FIG. 4A is the replicating form of AAV; lanes 2–5 show D1H, D1B, D1C and D1A of Example 1 in the presence of rep; lanes 5 and 6 show D1A and D1C in the absence of rep. Hirt extracts from the 293 cells infected with putative Ad.AV.CMVLacZ hybrid clones D1A and D1c revealed a single band corresponding to the viral DNA, when probed with a LacZ restriction fragment (FIG. 4A). In the presence of rep proteins 78 and 52, however, the same clones yielded a banding pattern that included not only the adenovirus DNA, but an RF monomer and dimer of AV.CMVLacZ (FIG. 4A). A single-stranded form of AV.CMVLacZ [SEQ ID NO: 1] was not evident. Two additional clones that gave similar banding patterns D1B and D1H, are also shown in FIG. 4A. In all, each of the eight Ad.AV.CMVLacZ hybrids that were found in FIG. 3 to express high levels of Lac Z activity were positive for rescue of the AAV domain.

With the exception of an extra band of approximately 3.5 kb (FIG. 4A), the rescue of the AV.CMVLacZ [SEQ ID NO: 1] from the hybrid viral DNA was nearly identical to results obtained from a standard cis and trans plasmid-based approach (FIG. 4B). In these later samples, adenovirus helper function was provided by pre-infecting cells with either wild-type Ad5 or an E1-deleted recombinant vector Ad.CBhpAP. The Ad.CBhpAP vector has the same sequence as the Ad.CMhpAP vector described above, except that the CMV promoter sequence is replaced by the chicken cytoplasmic β-actin promoter [nucleotides +1 to +275 as described in T. A. Kost et al, *Nucl. Acids Res.*, 11(23):8287 (1983)]. The level of rescue in cells infected with WT Ad5 appeared to be greater relative to those infected with the recombinant Ad.CBhpAP virus, likely due to the additional E1 expression provided by the wild-type genome. The relevance of including an E1 deleted adenovirus here is to document that the level of adenovirus E1 proteins expressed in 293 cells is sufficient for AAV helper function.

EXAMPLE 3

Synthesis of Polylysine Conjugates

Figure 9:
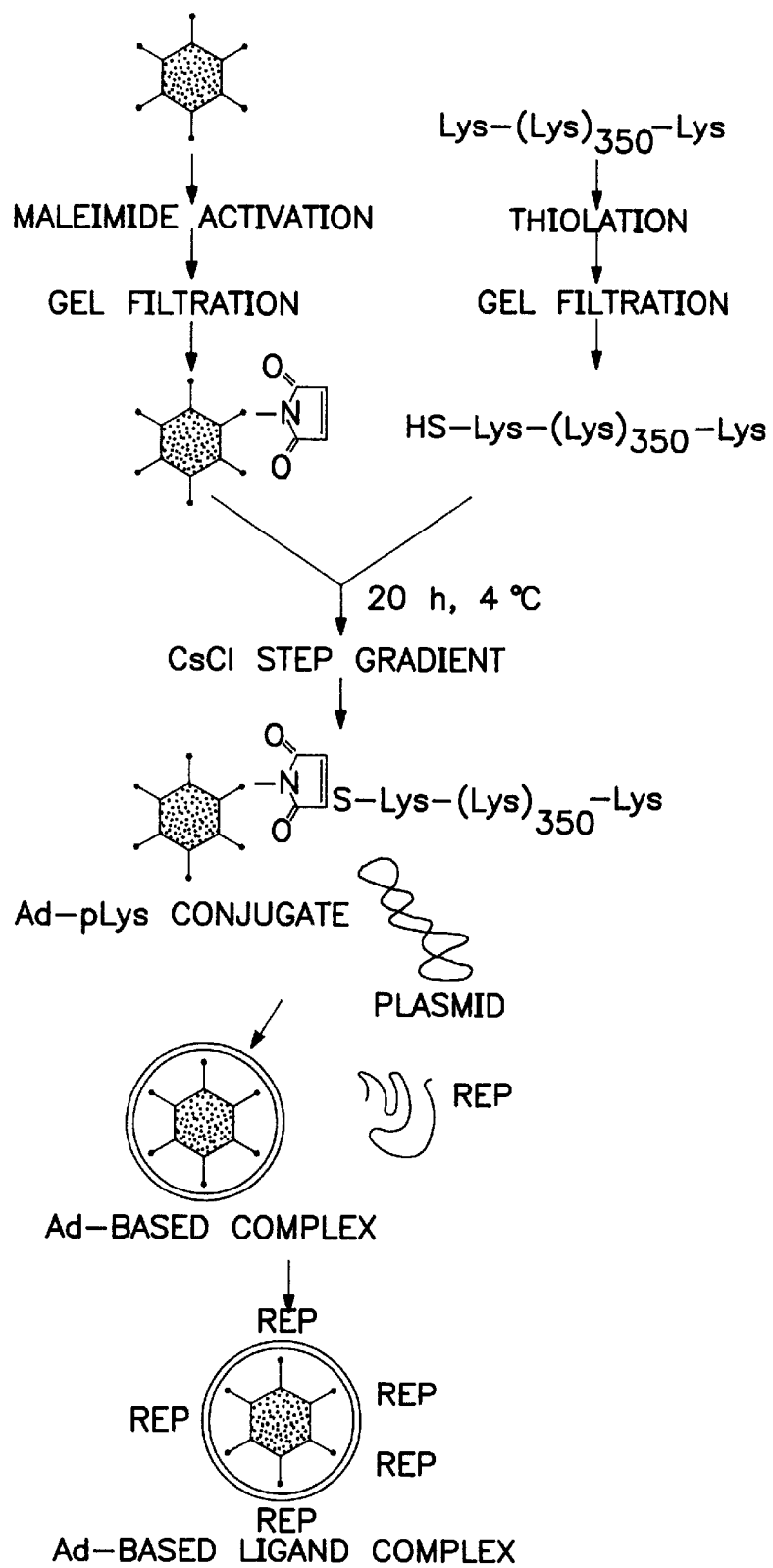
FIG. 9 is a flow diagram of the construction of a hybrid conjugate formed by a hybrid vector construct, a poly-L-lysine sequence and attached AAV rep-containing plasmid.

Another version of the vector of this invention is a polylysine conjugate with a rep plasmid complexed directly to the hybrid capsid. This conjugate permits efficient delivery of the rep expression plasmid pRep78/52 [SEQ ID NO: 2] in tandem with the hybrid virus, thereby removing the need for a separate transfection step. See, FIG. 9 for a diagrammatic outline of this construction.

Purified stocks of a large-scale expansion of Ad.AV.CM-VLacZ clone D1A were modified by coupling poly-L-lysine to the virion capsid essentially as described by K. J. Fisher and J. M. Wilson, *Biochem. J.*, 299:49–58 (1994), resulting in an Ad.AV.CMVLacZ-(Lys)$_n$ conjugate. The procedure involves three steps. First, hybrid virions are activated through primary amines on capsid proteins with the heterobifunctional water-soluble cross-linking agent, sulpho-SMCC [sulpho-(N-succinimidyl 4-(N-maleimidomethyl)-cyclohexane-1-carboxylate] (Pierce). The conjugation reaction, which contained 0.5 mg (375 nmol) of sulpho-SMCC and $6 \times 10^{12}$ $A_{260}$ hybrid vector particles in 3.0 ml of HBS, was incubated at 30° C. for 45 minutes with constant gentle shaking. This step involved formation of a peptide bond between the active N-hydroxysuccinimide (NHS) ester of sulpho-SMCC and a free amine (e.g. lysine) contributed by an adenovirus protein sequence (capsid protein) in the vector, yielding a maleimide-activated viral particle.

Unincorporated, unreacted cross-linker was removed by gel filtration on a 1 cm×15 cm Bio-Gel P-6DG (Bio-Rad Laboratories) column equilibrated with 50 mM Tris/HCl buffer, pH 7.0, and 150 mM NaCl. Peak $A_{260}$ fractions containing maleimide-activated hybrid vector were combined and placed on ice.

Second, poly-L-lysine having a molecular mass of 58 kDa at 10 mg/ml in 50 mM triethanolamine buffer (pH 8.0), 150 mM NaCl and 1 mM EDTA was thiolated with 2-imminothiolane/HCl (Traut's Reagent; Pierce) to a molar ratio of 2 moles-SH/mole polylysine under $N_2$; the cyclic thioimidate reacts with the poly(L-lysine) primary amines resulting in a thiolated polycation. After a 45 minute incubation at room temperature the reaction was applied to a 1 cm×15 cm Bio-Gel P6DG column equilibrated with 50 mM Tris/HCl buffer (pH 7.0), 150 mM NaCl and 2 mM EDTA to remove unincorporated Traut's Reagent.

Quantification of free thiol groups was accomplished with Ellman's reagent [5,5'-dithio-bis-(2-nitrobenzoic acid)], revealing approximately 2 mol of —SH/mol of poly(L-lysine). The coupling reaction was initiated by adding $1 \times 10^{12}$ $A_{260}$ particles of maleimide-activated hybrid vector/mg of thiolated poly(L-lysine) and incubating the mixture on ice at 4° C. for 15 hours under argon. 2-mercaptoethylamine was added at the completion of the reaction and incubation carried out at room temperature for 20 minutes to block unreacted maleimide sites.

Virus-polylysine conjugates, Ad.AV.CMVLacZ-(Lys)$_n$, were purified away from unconjugated poly(L-lysine) by ultracentrifugation through a CsCl step gradient with an initial composition of equal volumes of 1.45 g/ml (bottom step) and 1.2 g/ml (top step) CsCl in 10 mM Tris/HCl buffer (pH 8.0). Centrifugation was at 90,000 g for 2 hours at 5° C. The final product was dialyzed against 20 mM Hepes buffer (pH 7.8) containing 150 mM NaCl (HBS).

Complexes of Ad.AV.CMVLacZ-(Lys), with pRep78/52 plasmid DNA [SEQ ID NO: 2] were formed by adding varying quantities of Ad.AV.CMVLacZ-(Lys)$_n$ in 50 μl HBS to 0.5 μg of pRep78/52 plasmid DNA [SEQ ID NO: 2] in 50 μl HBS. After 30 minutes incubation at room temperature, a complex was formed of the hybrid vector Ad.AV.CMVLacZ-(Lys)$_n$ associated in a single particle with the plasmid DNA containing the rep genes.

This complex was evaluated for DNA binding capacity by gel mobility shift assays performed as described in Fisher et al, cited above. This analysis revealed that the plasmid binding capacity of the purified conjugate (expressed as the number of A$_{260}$ particles Ad.AV.CMVLacZ-(Lys)$_n$ that can neutralize the charge contributed by 1 μg plasmid DNA) was 1 μg pRep78/52 plasmid DNA/6.0×10$^{10}$ A$_{260}$ particles Ad.AV.CMVLacZ-(Lys)$_n$.

EXAMPLE 4
Trans-Infection Protocol to Demonstrate AAV Excision and Amplification Trans-infection complexes were prepared by mixing Ad.AV.CMVLacZ-(Lys)$_n$ conjugate with pRep78/52 plasmid [SEQ ID NO: 2] and applied to 293 cells as follows. Ad.AV.CMVLacZ-(Lys)$_n$ (6×10$^{10}$ A$_{260}$ particles) in 100 μl DMEM was added dropwise to a microfuge tube containing 1 μg plasmid DNA in 100 μl DMEM. The mixture was gently mixed and allowed to incubate at room temperature for 10–15 minutes. The trans-infection cocktail was added to 293 cells seeded in a 35 mm 6-well as detailed above. Thirty hours later, cells were harvested and Hirt extracts prepared.

Samples were resolved on a 1.2% agarose gel and electroblotted onto a nylon membrane. Blots were hybridized (Southern) with a P-32 random primer-labeled restriction fragment isolated from the *E. coli* LacZ cDNA.

Figures 5A, 5B:
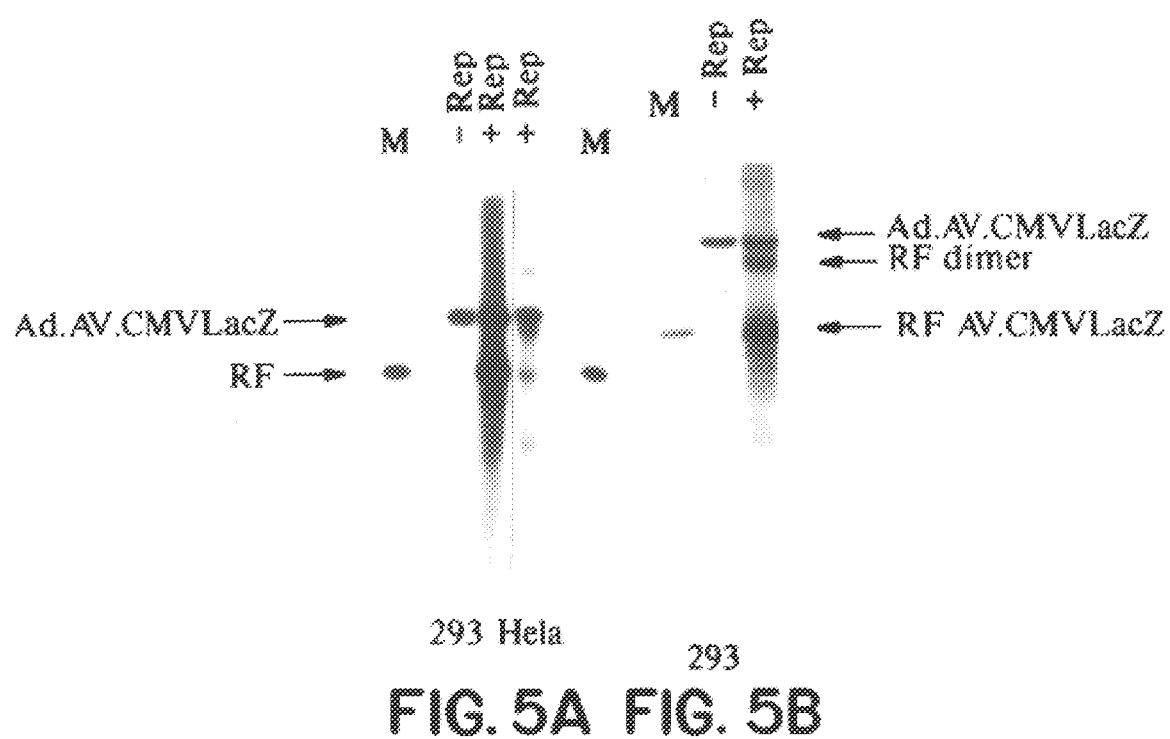
FIG. 5A is an autoradiogram demonstrating the rescue from cells transduced with the hybrid virus-molecular conjugate, Ad.AV.CMVLacZ-(Lys)$_n$. Lanes 1 and 5 are marker lanes showing the replicating form of AV.CMVLacZ. Lane 2 illustrates the results of trans-infection of 293 cells with the hybrid conjugate in the absence of a rep gene. Lane 3 illustrates rescue of the AV.CMVLacZ sequence [SEQ ID NO: 1] from 293 cells trans-infected with Ad.AV.CMVLacZ complexed with pRep78/52. Lane 4 illustrates the results of trans-infection of HeLa cells with Ad.AV.CMVLacZ complexed with pRep78/52.
FIG. 5B is an autoradiogram which duplicates the lanes 1–3 of FIG. 5A in 293 cells.

In the resulting autoradiogram (FIG. 5B), the Hirt extracts from 293 cells revealed a banding pattern that suggested the AV.CMVLacZ minigene sequence [SEQ ID NO: 1] was efficiently rescued from the hybrid conjugate (FIG. 5B, lane 3). Both an RF monomer and dimer of the recombinant AV.CMVLacZ sequence were evident. As was observed previously, the rescue event was dependent on rep proteins since 293 cells that were trans-infected with a hybrid conjugate complexed with an irrelevant plasmid (i.e. pCMVhpAP) revealed only Ad.AV.CMVLacZ DNA (FIG. 5B, lane 2). This negative control for rescue was secondarily useful for demonstrating the high efficiency of gene transfer to 293 cells that was achieved with the conjugate vehicle.

A duplicate set of 293 monolayers were fixed 24 hours after addition of the trans-infection cocktail and histochemically stained for LacZ as described in Price et al, cited above, or for alkaline phosphatase activity as described in J. H. Schreiber et al, *BioTechniques*, 14:818–823 (1993). Here LacZ was a marker for the Ad.AV.CMVLacZ hybrid, while alkaline phosphatase served as a reporter for the carrier plasmid. Greater than 90% of the monolayer was transduced with both LacZ and alkaline phosphatase transgenes, showing the high efficiency of the conjugate delivery vehicle (differential staining revealed a blue color for the hybrids containing the LacZ marker and a purple color for the plasmids bearing the AP marker).

Because of the important role E1 proteins have for progression of the AAV lifecycle, it was critical to test the efficiency of the hybrid delivery system in a setting where E1 proteins are not expressed. A trans-infection experiment using the hybrid conjugate complexed with pRep78/52 [SEQ ID NO: 2] was therefore conducted in HeLa cells [ATCC CCL2] to remove the involvement of E1 proteins. The findings suggested rescue of AV.CMVLacZ occurred evidenced by the accumulation of RF monomers and dimers. Rescue from HeLa cells (which unlike the 293 cells do not contain any adenovirus E1 proteins) revealed lower levels of rescue of the transgene [FIG. 5A, compare lane 4 (Hela) with lane 3 (293)]. The expression of rep from the AAV P5 promoter is upregulated by adenovirus E1 and signals the beginning of the AAV lytic cycle. In the absence of E1, rep expression from the P5 promoter is virtually silent which is important for maintenance of the proviral latent stages of the AAV lifecycle. It is anticipated that a promoter not dependent on E1 expression will upon substitution for P5, overcome this problem.

EXAMPLE 5
Integration of the Transgene

A preliminary study has been performed to determine whether the AAV sequence rescued from the hybrid vector can achieve provirus status in a target cell (FIG. 10). Briefly, HeLa cells [ATCC CCL 2] were infected with the hybrid conjugate complexed with pRep78/52 [SEQ ID NO: 2] and passaged until stable colonies of LacZ expressing cells were evident. A duplicate plate of cells was infected with the same conjugate, but instead of being complexed with the pRep78/52 plasmid [SEQ ID NO: 2], carried an irrelevant plasmid. These findings indicated that cells that received the Rep containing hybrid particle produced a greater number of stable LacZ positive colonies than cells that were infected with the control vector. Although this could be interpreted as a reflection of multiple rescue and integration events in cells that expressed Rep proteins, an episomal form of AAV that can persist for extended periods of time cannot be ruled out.

To establish the occurrence of integration into the chromosome of the minigene AV.CMVLacZ from the hybrid conjugate, the following experiment is performed. The Ad.AV.CMVLacZ-(Lys)$_n$ conjugate carrying pRep78/52 plasmid [SEQ ID NO: 2] is used to infect HeLa cells [ATCC CRL2] (primary fibroblasts may also be used). The infected cells are passaged for several generations. The cells are grown to confluency, split and allowed to grow to confluency again, split again and this cycle repeated as desired. This permits sufficient time for uptake, expression, replication and integration to occur. See FIG. 10.

To verify that the recombinant AAV sequence that was rescued from the hybrid genome (step III of FIG. 10) has integrated into a chromosome of the host cell (step IV of FIG. 10), cells are separated by a Fluorescence Activated Cell Sorter (FACS). By this technique, those cells containing a stable integrated copy of the recombinant AV.CMVLacZ minigene are separated based on the presence of the β-galactosidase reporter. These cells are tagged with fluorescein-labeled antibodies that recognize the β-Gal protein, and are then separated from non-transduced cells (i.e. those that did not receive a copy of the AAV minigene) by FACS.

DNA is isolated from this purified population of cells and used to construct a genomic library which is screened for individual clones and the sequence verified. If integration occurs, it is documented directly by sequence analysis.

EXAMPLE 6
Gene Transfer Vehicle for Cystic Fibrosis

An adenovirus-AAV-CFTR vector is constructed by modifying the hybrid Ad.AV.CMVlacZ vector described in Example 1 to contain the cystic fibrosis transmembrane regulator (CFTR) gene [J. R. Riordan et al, *Science*, 245:1066–1073 (1989)] in place of the lacZ gene, using known techniques. One suitable method involves producing a new vector using the techniques described in Example 1. In this new vector the LacZ minigene is replaced with the CFTR minigene. For performance of this method vectors bearing the CFTR gene have been previously described and can be readily constructed. This new or reconstructed vector is used to generate a new virus through homologous recombination as described above. The resulting hybrid vector is termed hybrid Ad.AV.CMVCFTR. It has the sequence of FIG. 2 [SEQ ID NO: 1], except that the LacZ gene is replaced with CFTR. Alternatively, the LacZ gene can be removed from the Ad.AV.CMVLacZ vector of Example 1 and replaced with the CFTR gene using known techniques.

This plasmid (or an analogous hybrid vector with a different promoter, regulatory regions, etc.) is useful in gene therapy alone, or preferably, in the form of a conjugate prepared as described in Example 4.

Treatment of cystic fibrosis, utilizing the vectors provided above, is particularly suited for in vivo, lung-directed, gene therapy. Airway epithelial cells are the most desirable targets for gene transfer because the pulmonary complications of CF are usually its most morbid and life-limiting. Thus, the hybrid vector of the invention, containing the CFTR gene, is delivered directly into the airway, e.g. by a formulating the hybrid vector above, into a preparation which can be inhaled. For example, the hybrid vector or conjugate of the invention containing the CFTR gene, is suspended in 0.25 molar sodium chloride. The vector or conjugate is taken up by respiratory airway cells and the gene is expressed.

Alternatively, the hybrid vectors or conjugates of the invention may be delivered by other suitable means, including site-directed injection of the vector bearing the CFTR gene. In the case of CFTR gene delivery, preferred solutions for bronchial instillation are sterile saline solutions containing in the range of from about $1\times10^7$ to $1\times10^{10}$ pfu/ml, more particularly, in the range of from about $1\times10^8$ to $1\times10^9$ pfu/ml of the viral vector of the present invention.

Other suitable methods for the treatment of cystic fibrosis by use of gene therapy vectors of this invention may be obtained from the art discussions of other types of gene therapy vectors for CF. See, for example, U. S. Pat. No. 5,240,846, incorporated by reference herein.

EXAMPLE 7
Gene Transfer Vehicle for Familial Hypercholesterolemia

Familial hypercholesterolemia (FH) is an autosomal dominant disorder caused by abnormalities (deficiencies) in the function or expression of LDL receptors [M. S. Brown and J. L. Goldstein, *Science*, 232(4746):34–37 (1986); J. L. Goldstein and M. S. Brown, "Familial hypercholesterolemia" in *Metabolic Basis of Inherited Disease*, ed. C. R. Scriver et al, McGraw Hill, New York, pp1215–1250 (1989) .] Patients who inherit one abnormal allele have moderate elevations in plasma LDL and suffer premature life-threatening coronary artery disease (CAD). Homozygous patients have severe hypercholesterolemia and life-threatening CAD in childhood.

A hybrid adenovirus-AAV-LDL vector of the invention is constructed by replacing the lacZ gene in the hybrid Ad.AV.CMVlacZ vector of Example 1 with an LDL receptor gene [T. Yamamoto et al, *Cell*, 39:27–38 (1984)] using known techniques and as described analogously for CF in the preceding example. Vectors bearing the LDL receptor gene can be readily constructed according to this invention. The resulting plasmid is termed hybrid pAd.AV.CMVLDL.

This plasmid is useful in gene therapy of FH alone, or preferably, in the form of a conjugate prepared as described in Example 4 to substitute a normal LDL gene for the abnormal allele responsible for the gene.

A. Ex Vivo Gene Therapy

Ex vivo gene therapy can be performed by harvesting and establishing a primary culture of hepatocytes from a patient. Known techniques may be used to isolate and transduce the hepatocytes with the above vector(s) bearing the LDL receptor gene(s). For example, techniques of collagenase perfusion developed for rabbit liver can be adapted for human tissue and used in transduction. Following transduction, the hepatocytes are removed from the tissue culture plates and reinfused into the patient using known techniques, e.g. via a catheter placed into the inferior mesenteric vein.

B. In Vivo Gene Therapy

Desirably, the in vivo approach to gene therapy, e.g. liver-directed, involves the use of the hybrid vectors and vector conjugates described above. A preferred treatment involves infusing a hybrid vector LDL conjugate of this invention into the peripheral circulation of the patient. The patient is then evaluated for change in serum lipids and liver tissues.

The hybrid virus or conjugate can be used to infect hepatocytes in vivo by direct injection into a peripheral or portal vein ($10^7$–$10^8$ pfu/kg) or retrograde into the biliary tract (same dose). This effects gene transfer into the majority of hepatocytes.

Treatments are repeated as necessary, e.g. weekly. Administration of a dose of virus equivalent to an MOI of approximately 20 (i.e. 20 pfu/hepatocyte) is anticipated to lead to high level gene expression in the majority of hepatocytes.

Figure 6A:
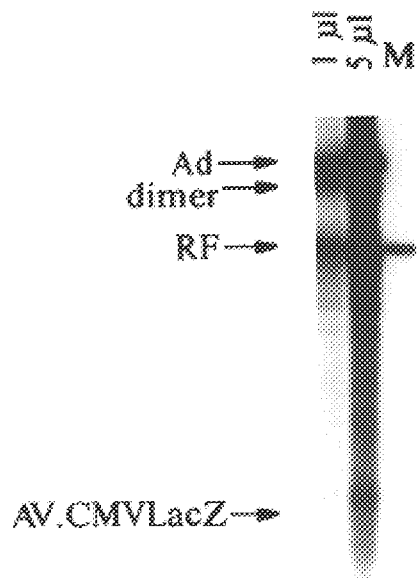
FIG. 6A is an autoradiogram demonstrating the rescue of AV.CMVLacZ following a trans-infection with Ad.AV.CMVLacZ-(Lys)$_n$ conjugated with pAdAAV using a 1 µl sample (lane 1) and a 5 µl sample (lane 2). Lane 3 is a marker.

EXAMPLE 8
Efficient Production of Recombinant AAV using A Hybrid Vector/Conjugate The following experiment demonstrated that the AAV genome that was rescued from the Ad.AV.CMVLacZ hybrid vector (FIGS. 4A, 6A and 6B) could be packaged into an AAV capsid, provided the cap open reading frame was supplied in trans. Thus the vectors of this invention are useful in a production method for recombinant AAV which overcomes the prior art complications that surround the high titer production of recombinant AAV.

A trans-infection complex was formed composed of the Ad.AV.CMVLacZ-(Lys)$_n$ conjugate described above and a transcomplementing plasmid pAdAAV, which is described in detail in R. J. Samulski et al, *J. Virol.*, 63(9):3822–3828 (1989)]. Briefly, plasmid pAdAAV encodes the entire rep and cap open reading frames in the absence of AAV ITRs, and has been shown to provide the necessary AAV helper functions for replication and packaging of recombinant AAV sequences.

Ad.AV.CMV$_{LacZ}$-(Lys)$_n$ conjugate ($1.5\times10^{13}$ A$_{260}$ particles) in 25 ml DMEM was added dropwise with constant gentle swirling in 25 ml DMEM containing 250 μg pAdAAV helper plasmid and incubated at room temperature for 10–15 minutes. The complex was diluted with 150 ml DMEM supplemented with 2% FBS and 20 ml aliquots were added to monolayers of 293 cells seeded on 150 mm plates. Forty hours post trans-infection, cells were harvested, suspended in 12 ml 10 mM Tris-Cl (pH 8.0), and stored at −80° C.

Because the anticipated outcome was the production of hybrid vector Ad.AV.CMVLacZ and a recombinant AAV virion (AV.CMVLacZ), both of which carry a functional LacZ minigene, it was not possible to use detection of LacZ activity as an indicator of AV.CMVLacZ production. A novel molecular approach was developed that could be performed in one day and permitted identification of the packaged viral DNAs.

Briefly, frozen cell suspensions were subjected to three rounds of freeze-thaw cycles to release recombinant AV.C-

MVLacZ and hybrid Ad.AV.CMVLacZ. On completion of the final thaw, micrococcal nuclease was added and the extract incubated at 37° C. for 30 minutes. Cell debris was removed by centrifugation (5000×g for 10 minutes) and the clarified supernatant (10 ml) applied to a 27 ml step gradient composed of equal volumes of CsCl at 1.2 g/ml, 1.36 g/ml, and 1.45 g/ml 10 mM Tris-Cl, pH8.0. Viral particles were banded at 25,000 rpm in a Beckman SW-28 rotor for 10 to 14 hours at 5° C. One ml fractions were collected from the bottom of the tube.

The fractions retrieved from the CsCl gradient of partially purified virus are then digested to release viral DNA from virion capsids as follows. A 5.0 μl sample of each fraction was transferred to a microfuge tube containing 20μl capsid digestion buffer (50 mM Tris-Cl, pH8.0, 1.0 mM EDTA, pH8,0, 0.5% SDS, and 1.0 mg/ml Proteinase K). The reaction was incubated at 50° C. for 1 hour, allowed to cool to room temperature, diluted with 10 μl milli-Q water, and agarose gel loading dye added.

These fractions are then analyzed by Southern blotting. Samples were resolved on a 1.2% agarose gel, electroblotted onto a nylon membrane. A P-32 labeled LacZ restriction fragment which was common to both vectors was used as a hybridization probe to locate the migration of viral DNA through the agarose gel. Viral bands were quantitated on a Molecular Dynamics Phosphoimager.

Figure 6B:
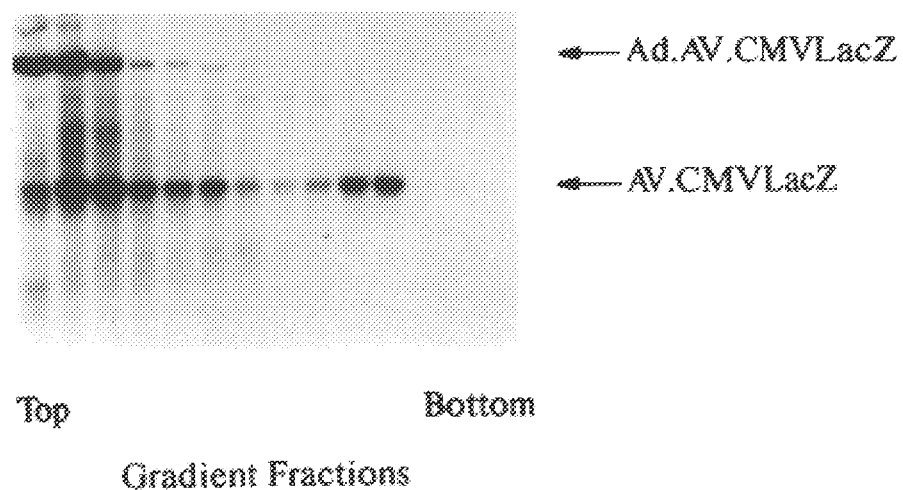
FIG. 6B is an autoradiogram illustrating a gradient pattern of AV.CMVLacZ of FIG. 6A.
Figure 7:
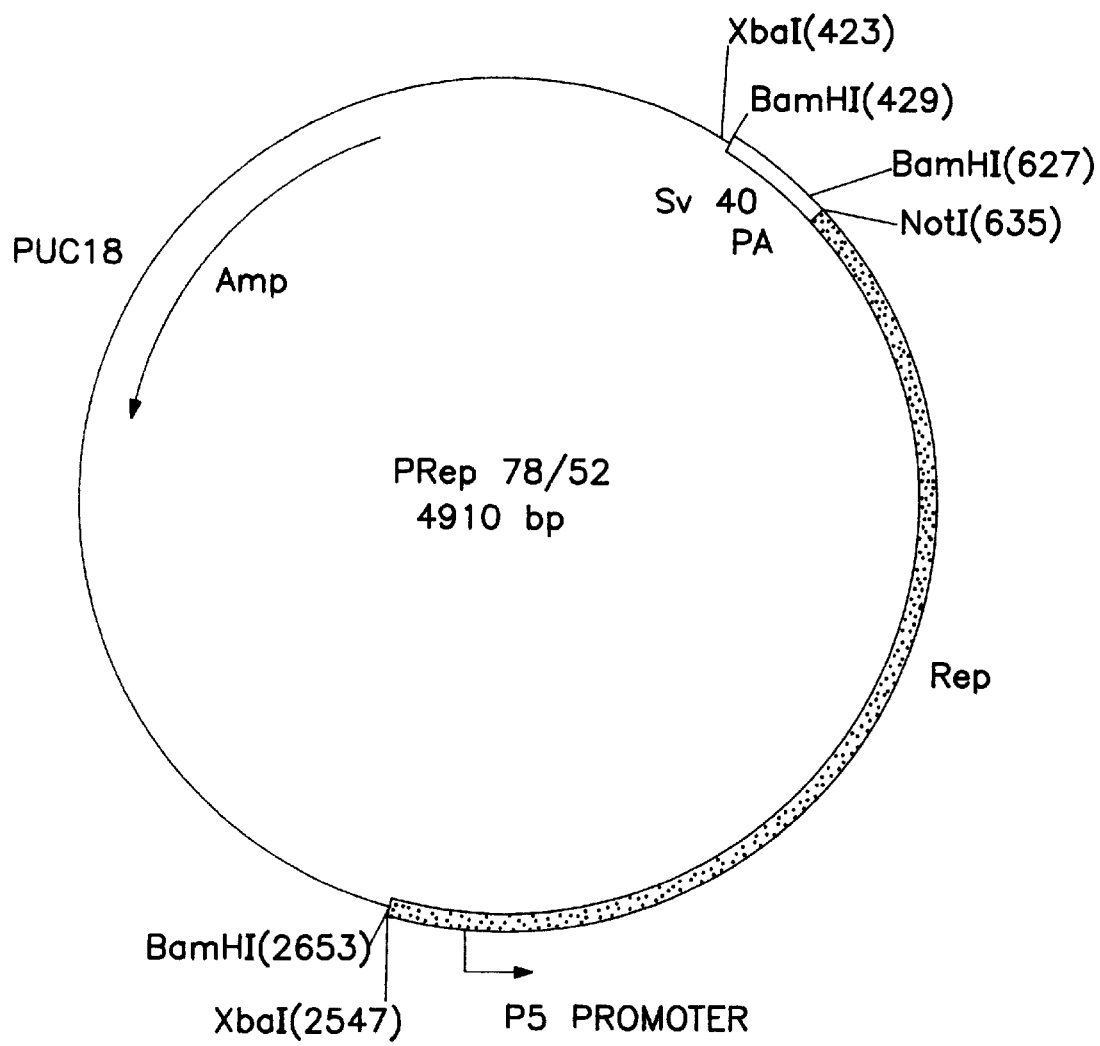
FIG. 7 is a schematic diagram of pRep78/52 [SEQ ID NO: 2]. This plasmid includes an AAV P5 promoter, Rep78, Rep52 and a poly-A sequence in a pUC18 plasmid background.

A sample of the extract before CsCl banding was also tested and revealed both hybrid Ad.AV.CMVLacZ DNA and double-stranded RF forms (monomers and dimers) of the rescued AV.CMVLacZ sequence [SEQ ID NO: 1] (FIG. 6A), a pattern similar to what is shown in FIG. 5B. A single-stranded monomer of AV.CMVLacZ appeared to be present in the crude extract; however, it was not until the virions were concentrated by buoyant density ultracentrifugation that the single-stranded genome became clearly evident (FIG. 6B). The recombinant virus was distributed over a range of CsCl densities and revealed a biphasic banding pattern. Quantitating the bands in FIG. 6B relative to previous AAV preparations that used adenovirus conjugate technology allowed estimation of the rAAV yield achieved with a hybrid Ad.AV.CMVLacZ-(Lys)$_n$ conjugate. This yield was significantly greater than yields of rAAV generated by conventional technology. This represents a significant improvement in rAAV production and indicates that the hybrid is useful for large-scale rAAV production.

All references recited above are incorporated herein by reference. Numerous modifications and variations of the present invention are included in the above-identified specification and are expected to be obvious to one of skill in the art. Such modifications and alterations to the compositions and processes of the present invention, such as those modifications permitting optimal use of the hybrid vectors as gene therapy vehicles or production vehicles for recombinant AAV production, are believed to be encompassed in the scope of the claims appended hereto.

What is claimed is:

1. A method for producing a recombinant adeno-associated virus comprising:
   (a) providing a hybrid viral vector comprising:
      (i) adenovirus sequences comprising the adenovirus 5' and 3' cis-elements necessary for replication and virion encapsidation; and
      (ii) adeno-associated virus sequences comprising the 5' and 3' ITRs of an adeno-associated virus, said adeno-associated virus sequences flanked by the adenoviral sequences of (i); and
      (iii) a selected gene operatively linked to regulatory sequences which direct expression of the selected gene in a target cell, said gene and regulatory sequences flanked by the adeno-associated virus sequences of (ii);
   (b) culturing a cell transfected with the vector of (a) and an optional helper virus in the presence of an AAV rep gene product; and
   (c) isolating from said culture a recombinant AAV.

2. A hybrid viral vector comprising:
   (a) adenovirus sequences comprising the adenovirus 5' and 3' cis-elements necessary for replication and virion encapsidation; and
   (b) adeno-associated virus sequences comprising the 5' and 3' ITRs of an adeno-associated virus, said adeno-associated virus sequences flanked by the adenoviral sequences of (a); and
   (c) a selected gene operatively linked to regulatory sequences which direct its expression in a target cell, said gene and regulatory sequences flanked by the adeno-associated virus sequences of (b).

3. The vector according to claim 2 wherein said adenovirus sequences further comprise a functional deletion in the E1 gene.

4. The vector according to claim 2 wherein said adenovirus sequences further comprise functional deletions in one or more adenovirus genes selected from the group consisting of: the E2a gene, the E4 gene, the late genes L1 through L5, and the intermediate genes IX and $IV_a$.

5. The vector according to claim 2 wherein said selected gene is a reporter gene.

6. The vector according to claim 2 further comprising an adeno-associated virus rep gene.

7. The vector according to claim 3 wherein said adenovirus sequences further comprise a functional deletion in the E3 gene.

8. The vector according to claim 5 wherein said reporter gene is selected from the group consisting of the genes encoding β-galactosidase, alkaline phosphatase and green fluorescent protein.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 10398 base pairs
( B ) TYPE: nucleic acid
( C ) STRANDEDNESS: double
( D ) TOPOLOGY: unknown ( i i ) MOLECULE TYPE: cDNA ( x i ) SEQUENCE DESCRIPTION: SEQ ID NO:1:

```
GAATTCGCTA  GCATCATCAA  TAATATACCT  TATTTTGGAT  TGAAGCCAAT  ATGATAATGA     60

GGGGGTGGAG  TTTGTGACGT  GGCGCGGGGC  GTGGGAACGG  GGCGGGTGAC  GTAGTAGTGT    120

GGCGGAAGTG  TGATGTTGCA  AGTGTGGCGG  AACACATGTA  AGCGACGGAT  GTGGCAAAAG    180

TGACGTTTTT  GGTGTGCGCC  GGTGTACACA  GGAAGTGACA  ATTTTCGCGC  GGTTTTAGGC    240

GGATGTTGTA  GTAAATTTGG  GCGTAACCGA  GTAAGATTTG  GCCATTTTCG  CGGGAAAACT    300

GAATAAGAGG  AAGTGAAATC  TGAATAATTT  TGTGTTACTC  ATAGCGCGTA  ATATTTGTCT    360

AGGGAGATCT  GCTGCGCGCT  CGCTCGCTCA  CTGAGGCCGC  CCGGGCAAAG  CCCGGGCGTC    420

GGGCGACCTT  TGGTCGCCCG  GCCTCAGTGA  GCGAGCGAGC  GCGCAGAGAG  GGAGTGGCCA    480

ACTCCATCAC  TAGGGGTTCC  TTGTAGTTAA  TGATTAACCC  GCCATGCTAC  TTATCTACAA    540

TTCGAGCTTG  CATGCCTGCA  GGTCGTTACA  TAACTTACGG  TAAATGGCCC  GCCTGGCTGA    600

CCGCCCAACG  ACCCCCGCCC  ATTGACGTCA  ATAATGACGT  ATGTTCCCAT  AGTAACGCCA    660

ATAGGGACTT  TCCATTGACG  TCAATGGGTG  GAGTATTTAC  GGTAAACTGC  CCACTTGGCA    720
```

-continued

| | | | | | |
|---|---|---|---|---|---|
|GTACATCAAG|TGTATCATAT|GCCAAGTACG|CCCCCTATTG|ACGTCAATGA|CGGTAAATGG| 780
|CCCGCCTGGC|ATTATGCCCA|GTACATGACC|TTATGGGACT|TTCCTACTTG|GCAGTACATC| 840
|TACGTATTAG|TCATCGCTAT|TACCATGGTG|ATGCGGTTTT|GGCAGTACAT|CAATGGGCGT| 900
|GGATAGCGGT|TTGACTCACG|GGGATTTCCA|AGTCTCCACC|CCATTGACGT|CAATGGGAGT| 960
|TTGTTTTGGC|ACCAAAATCA|ACGGGACTTT|CCAAAATGTC|GTAACAACTC|CGCCCATTG| 1020
|ACGCAAATGG|GCGGTAGGCG|TGTACGGTGG|GAGGTCTATA|TAAGCAGAGC|TCGTTTAGTG| 1080
|AACCGTCAGA|TCGCCTGGAG|ACGCCATCCA|CGCTGTTTTG|ACCTCCATAG|AAGACACCGG| 1140
|GACCGATCCA|GCCTCCGGAC|TCTAGAGGAT|CCGGTACTCG|AGGAACTGAA|AAACCAGAAA| 1200
|GTTAACTGGT|AAGTTTAGTC|TTTTTGTCTT|TTATTTCAGG|TCCCGGATCC|GGTGGTGGTG| 1260
|CAAATCAAAG|AACTGCTCCT|CAGTGGATGT|TGCCTTTACT|TCTAGGCCTG|TACGGAAGTG| 1320
|TTACTTCTGC|TCTAAAAGCT|GCGGAATTGT|ACCCGCGGCC|GCAATTCCCG|GGGATCGAAA| 1380
|GAGCCTGCTA|AAGCAAAAAA|GAAGTCACCA|TGTCGTTTAC|TTTGACCAAC|AAGAACGTGA| 1440
|TTTTCGTTGC|CGGTCTGGGA|GGCATTGGTC|TGGACACCAG|CAAGGAGCTG|CTCAAGCGCG| 1500
|ATCCCGTCGT|TTTACAACGT|CGTGACTGGG|AAAACCCTGG|CGTTACCCAA|CTTAATCGCC| 1560
|TTGCAGCACA|TCCCCCTTTC|GCCAGCTGGC|GTAATAGCGA|AGAGGCCCGC|ACCGATCGCC| 1620
|CTTCCCAACA|GTTGCGCAGC|CTGAATGGCG|AATGGCGCTT|TGCCTGGTTT|CCGGCACCAG| 1680
|AAGCGGTGCC|GGAAAGCTGG|CTGGAGTGCG|ATCTTCCTGA|GGCCGATACT|GTCGTCGTCC| 1740
|CCTCAAACTG|GCAGATGCAC|GGTTACGATG|CGCCCATCTA|CACCAACGTA|ACCTATCCCA| 1800
|TTACGGTCAA|TCCGCCGTTT|GTTCCCACGG|AGAATCCGAC|GGGTTGTTAC|TCGCTCACAT| 1860
|TTAATGTTGA|TGAAAGCTGG|CTACAGGAAG|GCCAGACGCG|AATTATTTTT|GATGGCGTTA| 1920
|ACTCGGCGTT|TCATCTGTGG|TGCAACGGGC|GCTGGGTCGG|TTACGGCCAG|GACAGTCGTT| 1980
|TGCCGTCTGA|ATTTGACCTG|AGCGCATTTT|TACGCGCCGG|AGAAAACCGC|CTCGCGGTGA| 2040
|TGGTGCTGCG|TTGGAGTGAC|GGCAGTTATC|TGGAAGATCA|GGATATGTGG|CGGATGAGCG| 2100
|GCATTTTCCG|TGACGTCTCG|TTGCTGCATA|AACCGACTAC|ACAAATCAGC|GATTTCCATG| 2160
|TTGCCACTCG|CTTTAATGAT|GATTTCAGCC|GCGCTGTACT|GGAGGCTGAA|GTTCAGATGT| 2220
|GCGGCGAGTT|GCGTGACTAC|CTACGGGTAA|CAGTTTCTTT|ATGGCAGGGT|GAAACGCAGG| 2280
|TCGCCAGCGG|CACCGCGCCT|TTCGGCGGTG|AAATTATCGA|TGAGCGTGGT|GGTTATGCCG| 2340
|ATCGCGTCAC|ACTACGTCTG|AACGTCGAAA|ACCCGAAACT|GTGGAGCGCC|GAAATCCCGA| 2400
|ATCTCTATCG|TGCGGTGGTT|GAACTGCACA|CCGCCGACGG|CACGCTGATT|GAAGCAGAAG| 2460
|CCTGCGATGT|CGGTTTCCGC|GAGGTGCGGA|TTGAAAATGG|TCTGCTGCTG|CTGAACGGCA| 2520
|AGCCGTTGCT|GATTCGAGGC|GTTAACCGTC|ACGAGCATCA|TCCTCTGCAT|GGTCAGGTCA| 2580
|TGGATGAGCA|GACGATGGTG|CAGGATATCC|TGCTGATGAA|GCAGAACAAC|TTTAACGCCG| 2640
|TGCGCTGTTC|GCATTATCCG|AACCATCCGC|TGTGGTACAC|GCTGTGCGAC|CGCTACGGCC| 2700
|TGTATGTGGT|GGATGAAGCC|AATATTGAAA|CCCACGGCAT|GGTGCCAATG|AATCGTCTGA| 2760
|CCGATGATCC|GCGCTGGCTA|CCGGCGATGA|GCGAACGCGT|AACGCGAATG|GTGCAGCGCG| 2820
|ATCGTAATCA|CCCGAGTGTG|ATCATCTGGT|CGCTGGGGAA|TGAATCAGGC|CACGGCGCTA| 2880
|ATCACGACGC|GCTGTATCGC|TGGATCAAAT|CTGTCGATCC|TTCCCGCCCG|GTGCAGTATG| 2940
|AAGGCGGCGG|AGCCGACACC|ACGGCCACCG|ATATTATTTG|CCCGATGTAC|GCGCGCGTGG| 3000
|ATGAAGACCA|GCCCTTCCCG|GCTGTGCCGA|AATGGTCCAT|CAAAAAATGG|CTTTCGCTAC| 3060
|CTGGAGAGAC|GCGCCCGCTG|ATCCTTTGCG|AATACGCCCA|CGCGATGGGT|AACAGTCTTG| 3120

-continued

| | | | | | | |
|---|---|---|---|---|---|---|
| GCGGTTTCGC | TAAATACTGG | CAGGCGTTTC | GTCAGTATCC | CCGTTTACAG | GGCGGCTTCG | 3180 |
| TCTGGGACTG | GGTGGATCAG | TCGCTGATTA | AATATGATGA | AAACGGCAAC | CCGTGGTCGG | 3240 |
| CTTACGGCGG | TGATTTTGGC | GATACGCCGA | ACGATGCCA | GTTCTGTATG | AACGGTCTGG | 3300 |
| TCTTTGCCGA | CCGCACGCCG | CATCCAGCGC | TGACGGAAGC | AAAACACCAG | CAGCAGTTTT | 3360 |
| TCCAGTTCCG | TTTATCCGGG | CAAACCATCG | AAGTGACCAG | CGAATACCTG | TTCCGTCATA | 3420 |
| GCGATAACGA | GCTCCTGCAC | TGGATGGTGG | CGCTGGATGG | TAAGCCGCTG | GCAAGCGGTG | 3480 |
| AAGTGCCTCT | GGATGTCGCT | CCACAAGGTA | AACAGTTGAT | TGAACTGCCT | GAACTACCGC | 3540 |
| AGCCGGAGAG | CGCCGGGCAA | CTCTGGCTCA | CAGTACGCGT | AGTGCAACCG | AACGCGACCG | 3600 |
| CATGGTCAGA | AGCCGGGCAC | ATCAGCGCCT | GGCAGCAGTG | GCGTCTGGCG | GAAAACCTCA | 3660 |
| GTGTGACGCT | CCCCGCCGCG | TCCCACGCCA | TCCGCATCT | GACCACCAGC | GAAATGGATT | 3720 |
| TTTGCATCGA | GCTGGGTAAT | AAGCGTTGGC | AATTTAACCG | CCAGTCAGGC | TTTCTTTCAC | 3780 |
| AGATGTGGAT | TGGCGATAAA | AAACAACTGC | TGACGCCGCT | GCGCGATCAG | TTCACCCGTG | 3840 |
| CACCGCTGGA | TAACGACATT | GGCGTAAGTG | AAGCGACCCG | CATTGACCCT | AACGCCTGGG | 3900 |
| TCGAACGCTG | GAAGGCGGCG | GGCCATTACC | AGGCCGAAGC | AGCGTTGTTG | CAGTGCACGG | 3960 |
| CAGATACACT | TGCTGATGCG | GTGCTGATTA | CGACCGCTCA | CGCGTGGCAG | CATCAGGGGA | 4020 |
| AAACCTTATT | TATCAGCCGG | AAAACCTACC | GGATTGATGG | TAGTGGTCAA | ATGGCGATTA | 4080 |
| CCGTTGATGT | TGAAGTGGCG | AGCGATACAC | CGCATCCGGC | GCGGATTGGC | CTGAACTGCC | 4140 |
| AGCTGGCGCA | GGTAGCAGAG | CGGGTAAACT | GGCTCGGATT | AGGGCCGCAA | GAAAACTATC | 4200 |
| CCGACCGCCT | TACTGCCGCC | TGTTTTGACC | GCTGGGATCT | GCCATTGTCA | GACATGTATA | 4260 |
| CCCCGTACGT | CTTCCCGAGC | GAAAACGGTC | TGCGCTGCGG | GACGCGCGAA | TTGAATTATG | 4320 |
| GCCCACACCA | GTGGCGCGGC | GACTTCCAGT | TCAACATCAG | CCGCTACAGT | CAACAGCAAC | 4380 |
| TGATGGAAAC | CAGCCATCGC | CATCTGCTGC | ACGCGGAAGA | AGGCACATGG | CTGAATATCG | 4440 |
| ACGGTTTCCA | TATGGGGATT | GGTGGCGACG | ACTCCTGGAG | CCCGTCAGTA | TCGGCGGAAT | 4500 |
| TACAGCTGAG | CGCCGGTCGC | TACCATTACC | AGTTGGTCTG | GTGTCAAAAA | TAATAATAAC | 4560 |
| CGGGCAGGCC | ATGTCTGCCC | GTATTTCGCG | TAAGGAAATC | CATTATGTAC | TATTTAAAAA | 4620 |
| ACACAAACTT | TTGGATGTTC | GGTTTATTCT | TTTTCTTTTA | CTTTTTTATC | ATGGGAGCCT | 4680 |
| ACTTCCCGTT | TTTCCCGATT | TGGCTACATG | ACATCAACCA | TATCAGCAAA | AGTGATACGG | 4740 |
| GTATTATTTT | TGCCGCTATT | TCTCTGTTCT | CGCTATTATT | CCAACCGCTG | TTTGGTCTGC | 4800 |
| TTTCTGACAA | ACTCGGCCTC | GACTCTAGGC | GGCCGCGGGG | ATCCAGACAT | GATAAGATAC | 4860 |
| ATTGATGAGT | TTGGACAAAC | CACAACTAGA | ATGCAGTGAA | AAAAATGCTT | TATTTGTGAA | 4920 |
| ATTTGTGATG | CTATTGCTTT | ATTTGTAACC | ATTATAAGCT | GCAATAAACA | AGTTAACAAC | 4980 |
| AACAATTGCA | TTCATTTTAT | GTTTCAGGTT | CAGGGGGAGG | TGTGGGAGGT | TTTTTCGGAT | 5040 |
| CCTCTAGAGT | CGAGTAGATA | AGTAGCATGG | CGGGTTAATC | ATTAACTACA | AGGAACCCCT | 5100 |
| AGTGATGGAG | TTGGCCACTC | CCTCTCTGCG | CGCTCGCTCG | CTCACTGAGG | CCGGGCGACC | 5160 |
| AAAGGTCGCC | CGACGCCCGG | GCTTTGCCCG | GGCGGCCTCA | GTGAGCGAGC | GAGCGCGCAG | 5220 |
| CAGATCTGGA | AGGTGCTGAG | GTACGATGAG | ACCCGCACCA | GGTGCAGACC | CTGCGAGTGT | 5280 |
| GGCGGTAAAC | ATATTAGGAA | CCAGCCTGTG | ATGCTGGATG | TGACCGAGGA | GCTGAGGCCC | 5340 |
| GATCACTTGG | TGCTGGCCTG | CACCCGCGCT | GAGTTTGGCT | CTAGCGATGA | AGATACAGAT | 5400 |
| TGAGGTACTG | AAATGTGTGG | GCGTGGCTTA | AGGGTGGGAA | AGAATATATA | AGGTGGGGGT | 5460 |
| CTTATGTAGT | TTTGTATCTG | TTTTGCAGCA | GCCGCCGCCG | CCATGAGCAC | CAACTCGTTT | 5520 |

-continued

| | | | | | | |
|---|---|---|---|---|---|---|
| GATGGAAGCA | TTGTGAGCTC | ATATTTGACA | ACGCGCATGC | CCCCATGGGC | CGGGGTGCGT | 5580 |
| CAGAATGTGA | TGGGCTCCAG | CATTGATGGT | CGCCCCGTCC | TGCCCGCAAA | CTCTACTACC | 5640 |
| TTGACCTACG | AGACCGTGTC | TGGAACGCCG | TTGGAGACTG | CAGCCTCCGC | CGCCGCTTCA | 5700 |
| GCCGCTGCAG | CCACCGCCCG | CGGGATTGTG | ACTGACTTTG | CTTTCCTGAG | CCCGCTTGCA | 5760 |
| AGCAGTGCAG | CTTCCCGTTC | ATCCGCCCGC | GATGACAAGT | TGACGGCTCT | TTTGGCACAA | 5820 |
| TTGGATTCTT | TGACCCGGGA | ACTTAATGTC | GTTCTCAGC | AGCTGTTGGA | TCTGCGCCAG | 5880 |
| CAGGTTTCTG | CCCTGAAGGC | TTCCTCCCCT | CCCAATGCGG | TTTAAAACAT | AAATAAAAAA | 5940 |
| CCAGACTCTG | TTTGGATTTG | GATCAAGCAA | GTGTCTTGCT | GTCTTTATTT | AGGGGTTTTG | 6000 |
| CGCGCGCGGT | AGGCCCGGGA | CCAGCGGTCT | CGGTCGTTGA | GGGTCCTGTG | TATTTTTTCC | 6060 |
| AGGACGTGGT | AAAGGTGACT | CTGGATGTTC | AGATACATGG | GCATAAGCCC | GTCTCTGGGG | 6120 |
| TGGAGGTAGC | ACCACTGCAG | AGCTTCATGC | TGCGGGGTGG | TGTTGTAGAT | GATCCAGTCG | 6180 |
| TAGCAGGAGC | GCTGGGCGTG | GTGCCTAAAA | ATGTCTTTCA | GTAGCAAGCT | GATTGCCAGG | 6240 |
| GGCAGGCCCT | TGGTGTAAGT | GTTTACAAAG | CGGTTAAGCT | GGGATGGGTG | CATACGTGGG | 6300 |
| GATATGAGAT | GCATCTTGGA | CTGTATTTTT | AGGTTGGCTA | TGTTCCCAGC | CATATCCCTC | 6360 |
| CGGGGATTCA | TGTTGTGCAG | AACCACCAGC | ACAGTGTATC | CGGTGCACTT | GGGAAATTTG | 6420 |
| TCATGTAGCT | TAGAAGGAAA | TGCGTGGAAG | AACTTGGAGA | CGCCCTTGTG | ACCTCCAAGA | 6480 |
| TTTTCCATGC | ATTCGTCCAT | AATGATGGCA | ATGGGCCCAC | GGGCGGCGGC | CTGGGCGAAG | 6540 |
| ATATTTCTGG | GATCACTAAC | GTCATAGTTG | TGTTCCAGGA | TGAGATCGTC | ATAGGCCATT | 6600 |
| TTTACAAAGC | GCGGGCGGAG | GGTGCCAGAC | TGCGGTATAA | TGGTTCCATC | CGGCCCAGGG | 6660 |
| GCGTAGTTAC | CCTCACAGAT | TTGCATTTCC | CACGCTTTGA | GTTCAGATGG | GGGGATCATG | 6720 |
| TCTACCTGCG | GGGCGATGAA | GAAAACGGTT | TCCGGGGTAG | GGGAGATCAG | CTGGGAAGAA | 6780 |
| AGCAGGTTCC | TGAGCAGCTG | CGACTTACCG | CAGCCGGTGG | GCCCGTAAAT | CACACCTATT | 6840 |
| ACCGGGTGCA | ACTGGTAGTT | AAGAGAGCTG | CAGCTGCCGT | CATCCCTGAG | CAGGGGGCC | 6900 |
| ACTTCGTTAA | GCATGTCCCT | GACTCGCATG | TTTTCCCTGA | CCAAATCCGC | CAGAAGGCGC | 6960 |
| TCGCCGCCCA | GCGATAGCAG | TTCTTGCAAG | GAAGCAAAGT | TTTTCAACGG | TTTGAGACCG | 7020 |
| TCCGCCGTAG | GCATGCTTTT | GAGCGTTTGA | CCAAGCAGTT | CCAGGCGGTC | CCACAGCTCG | 7080 |
| GTCACCTGCT | CTACGGCATC | TCGATCCAGC | ATATCTCCTC | GTTTCGCGGG | TTGGGGCGGC | 7140 |
| TTTCGCTGTA | CGGCAGTAGT | CGGTGCTCGT | CCAGACGGGC | CAGGGTCATG | TCTTTCCACG | 7200 |
| GGCGCAGGGT | CCTCGTCAGC | GTAGTCTGGG | TCACGGTGAA | GGGGTGCGCT | CCGGGCTGCG | 7260 |
| CGCTGGCCAG | GGTGCGCTTG | AGGCTGGTCC | TGCTGGTGCT | GAAGCGCTGC | CGGTCTTCGC | 7320 |
| CCTGCGCGTC | GGCCAGGTAG | CATTTGACCA | TGGTGTCATA | GTCCAGCCCC | TCCGCGGCGT | 7380 |
| GGCCCTTGGC | GCGCAGCTTG | CCCTTGGAGG | AGGCGCCGCA | CGAGGGCAG | TGCAGACTTT | 7440 |
| TGAGGGCGTA | GAGCTTGGGC | GCGAGAAATA | CCGATTCCGG | GGAGTAGGCA | TCCGCGCCGC | 7500 |
| AGGCCCCGCA | GACGGTCTCG | CATTCCACGA | GCCAGGTGAG | CTCTGGCCGT | TCGGGGTCAA | 7560 |
| AAACCAGGTT | TCCCCCATGC | TTTTTGATGC | GTTTCTTACC | TCTGGTTTCC | ATGAGCCGGT | 7620 |
| GTCCACGCTC | GGTGACGAAA | AGGCTGTCCG | TGTCCCCGTA | TACAGACTTG | AGAGGCCTGT | 7680 |
| CCTCGACCGA | TGCCCTTGAG | AGCCTTCAAC | CCAGTCAGCT | CCTTCCGGTG | GGCGCGGGGC | 7740 |
| ATGACTATCG | TCGCCGCACT | TATGACTGTC | TTCTTTATCA | TGCAACTCGT | AGGACAGGTG | 7800 |
| CCGGCAGCGC | TCTGGGTCAT | TTTCGGCGAG | GACCGCTTTC | GCTGGAGCGC | GACGATGATC | 7860 |
| GGCCTGTCGC | TTGCGGTATT | CGGAATCTTG | CACGCCCTCG | CTCAAGCCTT | CGTCACTGGT | 7920 |

```
CCCGCCACCA  AACGTTTCGG  CGAGAAGCAG  GCCATTATCG  CCGGCATGGC  GGCCGACGCG   7980
CTGGGCTACG  TCTTGCTGGC  GTTCGCGACG  CGAGGCTGGA  TGGCCTTCCC  CATTATGATT   8040
CTTCTCGCTT  CCGGCGGCAT  CGGGATGCCC  GCGTTGCAGG  CCATGCTGTC  CAGGCAGGTA   8100
GATGACGACC  ATCAGGGACA  GCTTCAAGGA  TCGCTCGCGG  CTCTTACCAG  CCTAACTTCG   8160
ATCACTGGAC  CGCTGATCGT  CACGGCGATT  TATGCCGCCT  CGGCGAGCAC  ATGGAACGGG   8220
TTGGCATGGA  TTGTAGGCGC  CGCCCTATAC  CTTGTCTGCC  TCCCCGCGTT  GCGTCGCGGT   8280
GCATGGAGCC  GGGCCACCTC  GACCTGAATG  GAAGCCGGCG  GCACCTCGCT  AACGGATTCA   8340
CCACTCCAAG  AATTGGAGCC  AATCAATTCT  TGCGGAGAAC  TGTGAATGCG  CAAACCAACC   8400
CTTGGCAGAA  CATATCCATC  GCGTCCGCCA  TCTCCAGCAG  CCGCACGCGG  CGCATCTCGG   8460
GCAGCGTTGG  GTCCTGGCCA  CGGGTGCGCA  TGATCGTGCT  CCTGTCGTTG  AGGACCCGGC   8520
TAGGCTGGCG  GGGTTGCCTT  ACTGGTTAGC  AGAATGAATC  ACCGATACGC  GAGCGAACGT   8580
GAAGCGACTG  CTGCTGCAAA  ACGTCTGCGA  CCTGAGCAAC  AACATGAATG  GTCTTCGGTT   8640
TCCGTGTTTC  GTAAAGTCTG  GAAACGCGGA  AGTCAGCGCC  CTGCACCATT  ATGTTCCGGA   8700
TCTGCATCGC  AGGATGCTGC  TGGCTACCCT  GTGGAACACC  TACATCTGTA  TTAACGAAGC   8760
CTTTCTCAAT  GCTCACGCTG  TAGGTATCTC  AGTTCGGTGT  AGGTCGTTCG  CTCCAAGCTG   8820
GGCTGTGTGC  ACGAACCCCC  CGTTCAGCCC  GACCGCTGCG  CCTTATCCGG  TAACTATCGT   8880
CTTGAGTCCA  ACCCGGTAAG  ACACGACTTA  TCGCCACTGG  CAGCAGCCAC  TGGTAACAGG   8940
ATTAGCAGAG  CGAGGTATGT  AGGCGGTGCT  ACAGAGTTCT  TGAAGTGGTG  GCCTAACTAC   9000
GGCTACACTA  GAAGGACAGT  ATTTGGTATC  TGCGCTCTGC  TGAAGCCAGT  TACCTTCGGA   9060
AAAAGAGTTG  GTAGCTCTTG  ATCCGGCAAA  CAAACCACCG  CTGGTAGCGG  TGGTTTTTTT   9120
GTTTGCAAGC  AGCAGATTAC  GCGCAGAAAA  AAAGGATCTC  AAGAAGATCC  TTTGATCTTT   9180
TCTACGGGGT  CTGACGCTCA  GTGGAACGAA  AACTCACGTT  AAGGGATTTT  GGTCATGAGA   9240
TTATCAAAAA  GGATCTTCAC  CTAGATCCTT  TTAAATTAAA  AATGAAGTTT  TAAATCAATC   9300
TAAAGTATAT  ATGAGTAAAC  TTGGTCTGAC  AGTTACCAAT  GCTTAATCAG  TGAGGCACCT   9360
ATCTCAGCGA  TCTGTCTATT  TCGTTCATCC  ATAGTTGCCT  GACTCCCCGT  CGTGTAGATA   9420
ACTACGATAC  GGGAGGGCTT  ACCATCTGGC  CCCAGTGCTG  CAATGATACC  GCGAGACCCA   9480
CGCTCACCGG  CTCCAGATTT  ATCAGCAATA  AACCAGCCAG  CCGGAAGGGC  CGAGCGCAGA   9540
AGTGGTCCTG  CAACTTTATC  CGCCTCCATC  CAGTCTATTA  ATTGTTGCCG  GGAAGCTAGA   9600
GTAAGTAGTT  CGCCAGTTAA  TAGTTTGCGC  AACGTTGTTG  CCATTGCTGC  AGGCATCGTG   9660
GTGTCACGCT  CGTCGTTTGG  TATGGCTTCA  TTCAGCTCCG  GTTCCCAACG  ATCAAGGCGA   9720
GTTACATGAT  CCCCCATGTT  GTGCAAAAAA  GCGGTTAGCT  CCTTCGGTCC  TCCGATCGTT   9780
GTCAGAAGTA  AGTTGGCCGC  AGTGTTATCA  CTCATGGTTA  TGGCAGCACT  GCATAATTCT   9840
CTTACTGTCA  TGCCATCCGT  AAGATGCTTT  TCTGTGACTG  GTGAGTACTC  AACCAAGTCA   9900
TTCTGAGAAT  AGTGTATGCG  GCGACCGAGT  TGCTCTTGCC  CGGCGTCAAC  ACGGGATAAT  9960
ACCGCGCCAC  ATAGCAGAAC  TTTAAAAGTG  CTCATCATTG  GAAAACGTTC  TTCGGGGCGA  10020
AAACTCTCAA  GGATCTTACC  GCTGTTGAGA  TCCAGTTCGA  TGTAACCCAC  TCGTGCACCC  10080
AACTGATCTT  CAGCATCTTT  TACTTTCACC  AGCGTTTCTG  GGTGAGCAAA  AACAGGAAGG  10140
CAAAATGCCG  CAAAAAAGGG  AATAAGGGCG  ACACGGAAAT  GTTGAATACT  CATACTCTTC  10200
CTTTTTCAAT  ATTATTGAAG  CATTTATCAG  GGTTATTGTC  TCATGAGCGG  ATACATATTT  10260
GAATGTATTT  AGAAAAATAA  ACAAATAGGG  GTTCCGCGCA  CATTTCCCCG  AAAAGTGCCA  10320
```

| | | | | | |
|---|---|---|---|---|---|
| CCTGACGTCT | AAGAAACCAT | TATTATCATG | ACATTAACCT | ATAAAAATAG | GCGTATCACG | 10380
| AGGCCCTTTC | GTCTTCAA | | | | | 10398

( 2 ) INFORMATION FOR SEQ ID NO:2:

( i ) SEQUENCE CHARACTERISTICS:
        ( A ) LENGTH: 4910 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:2:

| | | | | | |
|---|---|---|---|---|---|
| TCGCGCGTTT | CGGTGATGAC | GGTGAAAACC | TCTGACACAT | GCAGCTCCCG | GAGACGGTCA | 60
| CAGCTTGTCT | GTAAGCGGAT | GCCGGGAGCA | GACAAGCCCG | TCAGGGCGCG | TCAGCGGGTG | 120
| TTGGCGGGTG | TCGGGGCTGG | CTTAACTATG | CGGCATCAGA | GCAGATTGTA | CTGAGAGTGC | 180
| ACCATATGCG | GTGTGAAATA | CCGCACAGAT | GCGTAAGGAG | AAAATACCGC | ATCAGGCGCC | 240
| ATTCGCCATT | CAGGCTGCGC | AACTGTTGGG | AAGGGCGATC | GGTGCGGGCC | TCTTCGCTAT | 300
| TACGCCAGCT | GGCGAAAGGG | GGATGTGCTG | CAAGGCGATT | AAGTTGGGTA | ACGCCAGGGT | 360
| TTTCCCAGTC | ACGACGTTGT | AAAACGACGG | CCAGTGCCAA | GCTTGCATGC | CTGCAGGTCG | 420
| ACTCTAGAGG | ATCCGAAAAA | ACCTCCCACA | CCTCCCCCTG | AACCTGAAAC | ATAAAATGAA | 480
| TGCAATTGTT | GTTGTTAACT | TGTTTATTGC | AGCTTATAAT | GGTTACAAAT | AAAGCAATAG | 540
| CATCACAAAT | TTCACAAATA | AAGCATTTTT | TTCACTGCAT | TCTAGTTGTG | GTTTGTCCAA | 600
| ACTCATCAAT | GTATCTTATC | ATGTCTGGAT | CCCCGCGGCC | GCCAAATCAT | TTATTGTTCA | 660
| AAGATGCAGT | CATCCAAATC | CACATTGACC | AGATCGCAGG | CAGTGCAAGC | GTCTGGCACC | 720
| TTTCCCATGA | TATGATGAAT | GTAGCACAGT | TTCTGATACG | CCTTTTTGAC | GACAGAAACG | 780
| GGTTGAGATT | CTGACACGGG | AAAGCACTCT | AAACAGTCTT | TCTGTCCGTG | AGTGAAGCAG | 840
| ATATTTGAAT | TCTGATTCAT | TCTCTCGCAT | TGTCTGCAGG | GAAACAGCAT | CAGATTCATG | 900
| CCCACGTGAC | GAGAACATTT | GTTTTGGTAC | CTGTCTGCGT | AGTTGATCGA | AGCTTCCGCG | 960
| TCTGACGTCG | ATGGCTGCGC | AACTGACTCG | CGCACCCGTT | TGGGCTCACT | TATATCTGCG | 1020
| TCACTGGGGG | CGGGTCTTTT | CTTGGCTCCA | CCCTTTTTGA | CGTAGAATTC | ATGCTCCACC | 1080
| TCAACCACGT | GATCCTTTGC | CCACCGGAAA | AAGTCTTTGA | CTTCCTGCTT | GGTGACCTTC | 1140
| CCAAAGTCAT | GATCCAGACG | GCGGGTGAGT | TCAAATTTGA | ACATCCGGTC | TTGCAACGGC | 1200
| TGCTGGTGTT | CGAAGGTCGT | TGAGTTCCCG | TCAATCACGG | CGCACATGTT | GGTGTTGGAG | 1260
| GTGACGATCA | CGGGAGTCGG | GTCTATCTGG | GCCGAGGACT | TGCATTTCTG | GTCCACGCGC | 1320
| ACCTTGCTTC | CTCCGAGAAT | GGCTTTGGCC | GACTCCACGA | CCTTGGCGGT | CATCTTCCCC | 1380
| TCCTCCCACC | AGATCACCAT | CTTGTCGACA | CAGTCGTTGA | AGGGAAAGTT | CTCATTGGTC | 1440
| CAGTTTACGC | ACCCGTAGAA | GGGCACAGTG | TGGGCTATGG | CCTCCGCGAT | GTTGGTCTTC | 1500
| CCGGTAGTTG | CAGGCCCAAA | CAGCCAGATG | GTGTTCCTCT | TGCCGAACTT | TTTCGTGGCC | 1560
| CATCCCAGAA | AGACGGAAGC | CGCATATTGG | GGATCGTACC | CGTTTAGTTC | CAAAATTTTA | 1620
| TAAATCGAT | TGCTGGAAAT | GTCCTCCACG | GGCTGCTGGC | CCACCAGGTA | GTCGGGGCG | 1680
| GTTTTAGTCA | GGCTCATAAT | CTTTCCCGCA | TTGTCCAAGG | CAGCCTTGAT | TTGGGACCGC | 1740
| GAGTTGGAGG | CCGCATTGAA | GGAGATGTAT | GAGGCCTGGT | CCTCCTGGAT | CCACTGCTTC | 1800
| TCCGAGGTAA | TCCCCTTGTC | CACGAGCCAC | CCGACCAGCT | CCATGTACCT | GGCTGAAGTT | 1860
| TTTGATCTGA | TCACCGGCGC | ATCAGAATTG | GGATTCTGAT | TCTCTTTGTT | CTGCTCCTGC | 1920

```
GTCTGCGACA CGTGCGTCAG ATGCTGCGCC ACCAACCGTT TACGCTCCGT GAGATTCAAA   1980
CAGGCGCTTA AATACTGTTC CATATTAGTC CACGCCCACT GGAGCTCAGG CTGGGTTTTG   2040
GGGAGCAAGT AATTGGGGAT GTAGCACTCA TCCACCACCT TGTTCCCGCC TCCGGCGCCA   2100
TTTCTGGTCT TTGTGACCGC GAACCAGTTT GGCAAAGTCG GCTCGATCCC GCGGTAAATT   2160
CTCTGAATCA GTTTTCGCG AATCTGACTC AGGAAACGTC CCAAAACCAT GGATTTCACC    2220
CCGGTGGTTT CCACGAGCAC GTGCATGTGG AAGTAGCTCT CTCCCTTCTC AAATTGCACA   2280
AAGAAAAGGG CCTCCGGGGC CTTACTCACA CGGCGCCATT CCGTCAGAAA GTCGCGCTGC   2340
AGCTTCTCGG CCACGGTCAG GGGTGCCTGC TCAATCAGAT TCAGATCCAT GTCAGAATCT   2400
GGCGGCAACT CCCATTCCTT CTCGGCCACC CAGTTCACAA AGCTGTCAGA AATGCCGGGC   2460
AGATGCCCGT CAAGGTCGCT GGGGACCTTA ATCACAATCT CGTAAACCCC GGCATGGCG    2520
GCTGCGCGTT CAAACCTCCC GCTTCAAAAT GGAGACCCTG CGTGCTCACT CGGGCTTAAA   2580
TACCCAGCGT GACCACATGG TGTCGCAAAA TGTCGCAAAA CACTCACGTG ACCTCTAATA   2640
CAGGACTCTA GAGGATCCCC GGGTACCGAG CTCGAATTCG TAATCATGGT CATAGCTGTT   2700
TCCTGTGTGA AATTGTTATC CGCTCACAAT TCCACACAAC ATACGAGCCG GAAGCATAAA   2760
GTGTAAAGCC TGGGGTGCCT AATGAGTGAG CTAACTCACA TTAATTGCGT TGCGCTCACT   2820
GCCCGCTTTC CAGTCGGGAA ACCTGTCGTG CCAGCTGCAT TAATGAATCG GCCAACGCGC   2880
GGGGAGAGGC GGTTTGCGTA TTGGGCGCTC TTCCGCTTCC TCGCTCACTG ACTCGCTGCG   2940
CTCGGTCGTT CGGCTGCGGC GAGCGGTATC AGCTCACTCA AAGGCGGTAA TACGGTTATC   3000
CACAGAATCA GGGGATAACG CAGGAAAGAA CATGTGAGCA AAAGGCCAGC AAAAGGCCAG   3060
GAACCGTAAA AAGGCCGCGT TGCTGGCGTT TTTCCATAGG CTCCGCCCCC CTGACGAGCA   3120
TCACAAAAAT CGACGCTCAA GTCAGAGGTG GCGAAACCCG ACAGGACTAT AAAGATACCA   3180
GGCGTTTCCC CCTGGAAGCT CCCTCGTGCG CTCTCCTGTT CCGACCCTGC CGCTTACCGG   3240
ATACCTGTCC GCCTTTCTCC CTTCGGGAAG CGTGGCGCTT TCTCATAGCT CACGCTGTAG   3300
GTATCTCAGT TCGGTGTAGG TCGTTCGCTC CAAGCTGGGC TGTGTGCACG AACCCCCCGT   3360
TCAGCCCGAC CGCTGCGCCT TATCCGGTAA CTATCGTCTT GAGTCCAACC CGGTAAGACA   3420
CGACTTATCG CCACTGGCAG CAGCCACTGG TAACAGGATT AGCAGAGCGA GGTATGTAGG   3480
CGGTGCTACA GAGTTCTTGA AGTGGTGGCC TAACTACGGC TACACTAGAA GGACAGTATT   3540
TGGTATCTGC GCTCTGCTGA AGCCAGTTAC CTTCGGAAAA AGAGTTGGTA GCTCTTGATC   3600
CGGCAAACAA ACCACCGCTG GTAGCGGTGG TTTTTTTGTT TGCAAGCAGC AGATTACGCG   3660
CAGAAAAAAA GGATCTCAAG AAGATCCTTT GATCTTTTCT ACGGGGTCTG ACGCTCAGTG   3720
GAACGAAAAC TCACGTTAAG GGATTTTGGT CATGAGATTA TCAAAAGGA TCTTCACCTA    3780
GATCCTTTTA AATTAAAAAT GAAGTTTTAA ATCAATCTAA AGTATATATG AGTAAACTTG   3840
GTCTGACAGT TACCAATGCT TAATCAGTGA GGCACCTATC TCAGCGATCT GTCTATTTCG   3900
TTCATCCATA GTTGCCTGAC TCCCCGTCGT GTAGATAACT ACGATACGGG AGGGCTTACC   3960
ATCTGGCCCC AGTGCTGCAA TGATACCGCG AGACCCACGC TCACCGGCTC CAGATTTATC   4020
AGCAATAAAC CAGCCAGCCG GAAGGGCCGA GCGCAGAAGT GGTCCTGCAA CTTTATCCGC   4080
CTCCATCCAG TCTATTAATT GTTGCCGGGA AGCTAGAGTA AGTAGTTCGC CAGTTAATAG   4140
TTTGCGCAAC GTTGTTGCCA TTGCTACAGG CATCGTGGTG TCACGCTCGT CGTTTGGTAT   4200
GGCTTCATTC AGCTCCGGTT CCCAACGATC AAGGCGAGTT ACATGATCCC CCATGTTGTG   4260
CAAAAAAGCG GTTAGCTCCT TCGGTCCTCC GATCGTTGTC AGAAGTAAGT TGGCCGCAGT   4320
```

| | | | | | | |
|---|---|---|---|---|---|---|
|GTTATCACTC|ATGGTTATGG|CAGCACTGCA|TAATTCTCTT|ACTGTCATGC|CATCCGTAAG|4380|
|ATGCTTTTCT|GTGACTGGTG|AGTACTCAAC|CAAGTCATTC|TGAGAATAGT|GTATGCGGCG|4440|
|ACCGAGTTGC|TCTTGCCCGG|CGTCAATACG|GGATAATACC|GCGCCACATA|GCAGAACTTT|4500|
|AAAAGTGCTC|ATCATTGGAA|AACGTTCTTC|GGGGCGAAAA|CTCTCAAGGA|TCTTACCGCT|4560|
|GTTGAGATCC|AGTTCGATGT|AACCCACTCG|TGCACCCAAC|TGATCTTCAG|CATCTTTTAC|4620|
|TTTCACCAGC|GTTTCTGGGT|GAGCAAAAAC|AGGAAGGCAA|AATGCCGCAA|AAAAGGGAAT|4680|
|AAGGGCGACA|CGGAAATGTT|GAATACTCAT|ACTCTTCCTT|TTTCAATATT|ATTGAAGCAT|4740|
|TTATCAGGGT|TATTGTCTCA|TGAGCGGATA|CATATTTGAA|TGTATTTAGA|AAAATAAACA|4800|
|AATAGGGGTT|CCGCGCACAT|TTCCCCGAAA|AGTGCCACCT|GACGTCTAAG|AAACCATTAT|4860|
|TATCATGACA|TTAACCTATA|AAAATAGGCG|TATCACGAGG|CCCTTTCGTC| |4910|